(12) United States Patent
Boveja

(10) Patent No.: US 6,356,788 B2
(45) Date of Patent: Mar. 12, 2002

(54) APPARATUS AND METHOD FOR ADJUNCT (ADD-ON) THERAPY FOR DEPRESSION, MIGRAINE, NEUROPSYCHIATRIC DISORDERS, PARTIAL COMPLEX EPILEPSY, GENERALIZED EPILEPSY AND INVOLUNTARY MOVEMENT DISORDERS UTILIZING AN EXTERNAL STIMULATOR

(76) Inventor: Birinder Bob Boveja, 8879 S. Chestnut Hill Way, Highlands Ranch, CO (US) 80130

( * ) Notice: Subject to any disclaimer, the term of this patent is extended or adjusted under 35 U.S.C. 154(b) by 0 days.

(21) Appl. No.: 09/727,570

(22) Filed: Nov. 30, 2000

Related U.S. Application Data

(63) Continuation-in-part of application No. 09/178,060, filed on Oct. 26, 1998, now Pat. No. 6,206,359.

(51) Int. Cl.$^7$ ................................................. A61N 1/36
(52) U.S. Cl. ........................................................ 607/45
(58) Field of Search ............................................ 607/45

(56) References Cited

U.S. PATENT DOCUMENTS 5,441,528 A * 8/1995 Chang et al. .................. 607/45

FOREIGN PATENT DOCUMENTS

DE 2533360 A1 * 2/1977 .................. 607/45

* cited by examiner

Primary Examiner—William E. Kamm
(74) Attorney, Agent, or Firm—Sheridan Ross P.C.

(57) ABSTRACT

An apparatus and method for adjunct (add-on) therapy of depression, migraine, neuropsychiatric disorders, partial complex epilepsy, generalized epilepsy and involuntary movement disorders comprises an implantable lead-receiver, and an external stimulator having controlling circuitry, a power source, and a coil to inductively couple the stimulator to the lead-receiver. The external stimulator emits electrical pulses to stimulate a cranial nerve such as the left vagus nerve according to a predetermined program. In a second mode of operation, an operator may manually override the predetermined sequence of stimulation.

25 Claims, 19 Drawing Sheets

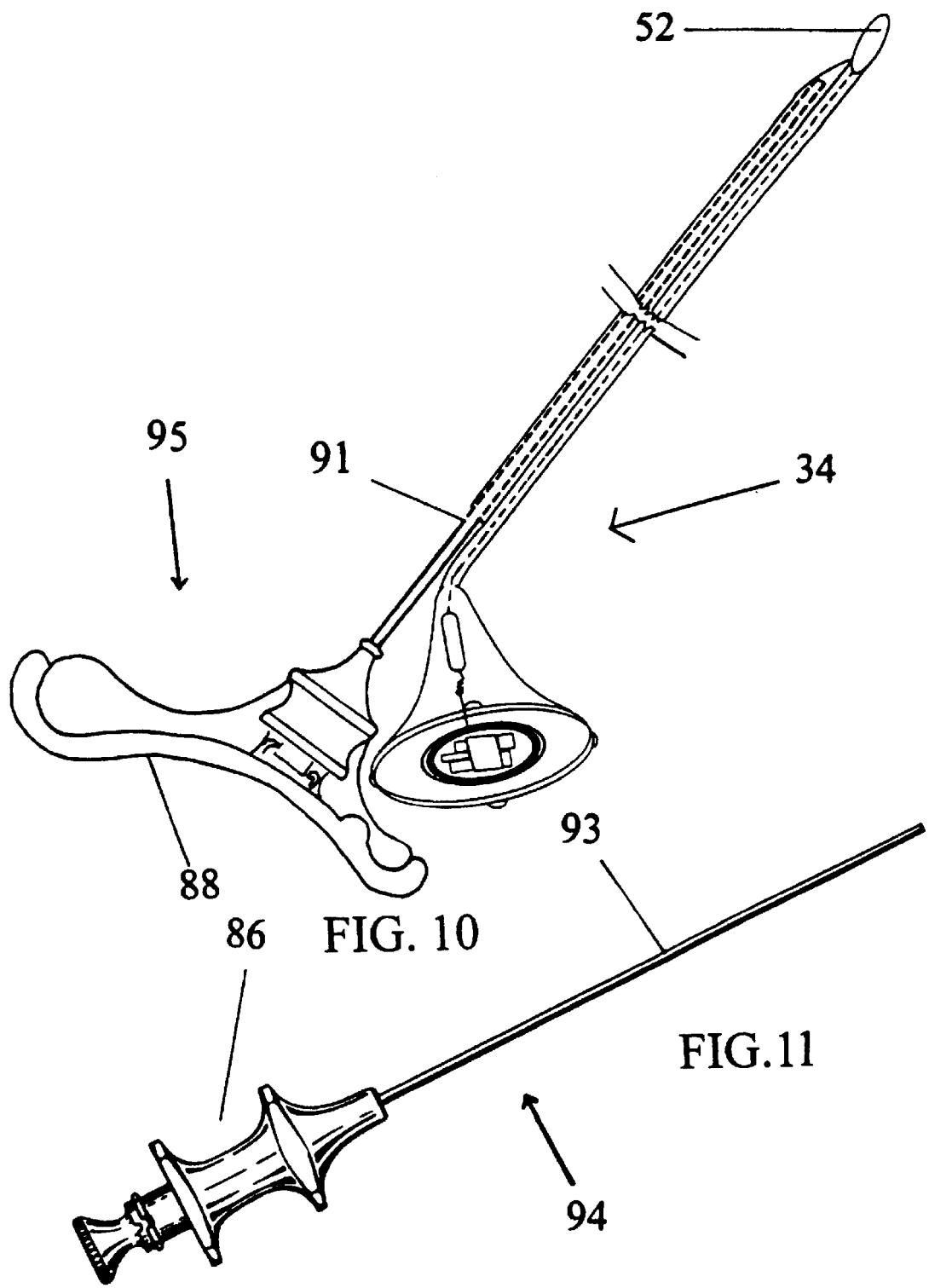

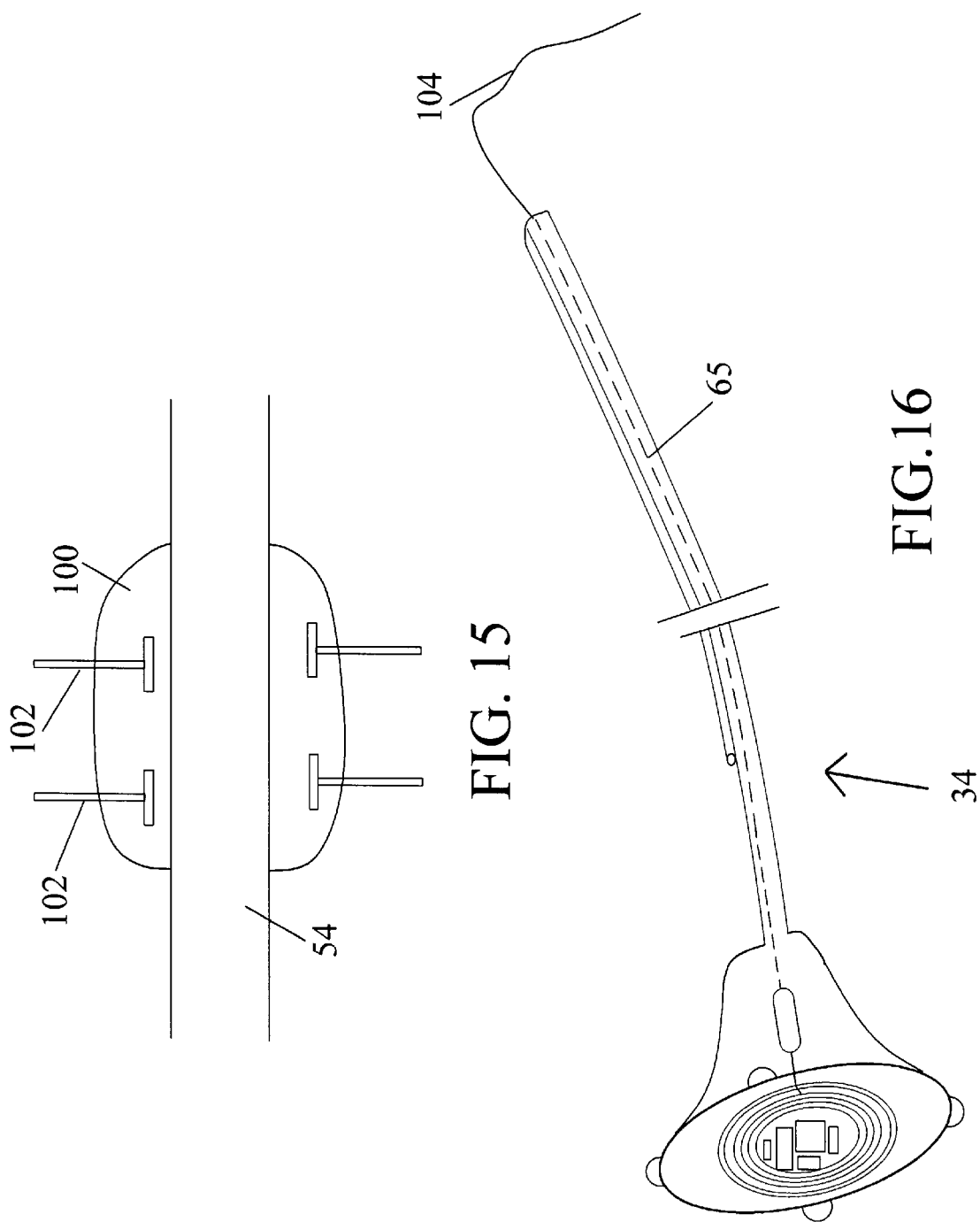

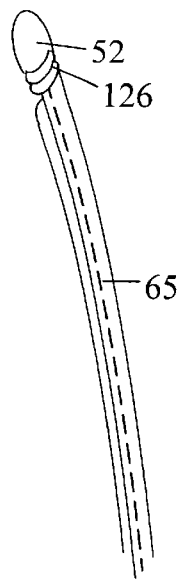
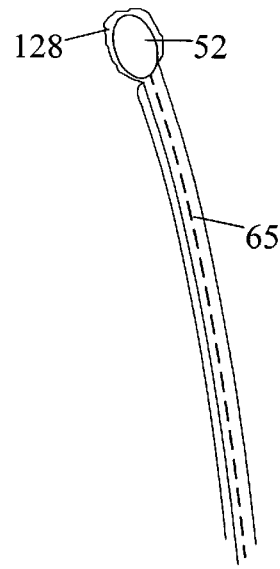
FIG. 21  FIG. 22
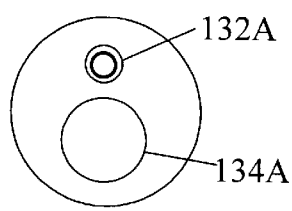
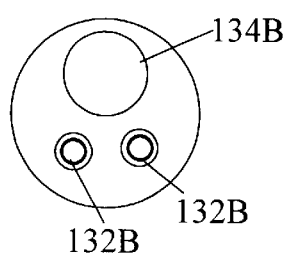
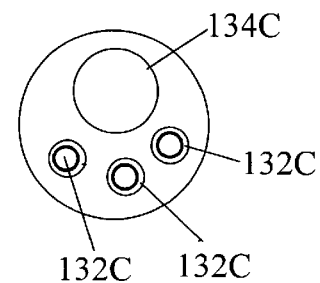
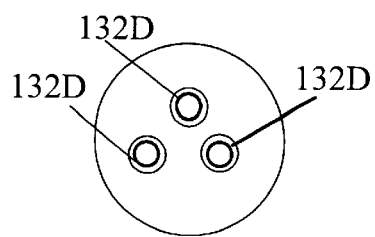
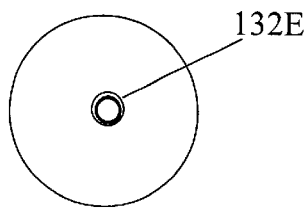
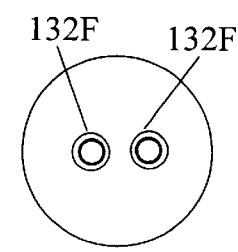
FIG.23

APPARATUS AND METHOD FOR ADJUNCT (ADD-ON) THERAPY FOR DEPRESSION, MIGRAINE, NEUROPSYCHIATRIC DISORDERS, PARTIAL COMPLEX EPILEPSY, GENERALIZED EPILEPSY AND INVOLUNTARY MOVEMENT DISORDERS UTILIZING AN EXTERNAL STIMULATOR

This is a Continuation-in-Part application claiming priority from prior application Ser. No. 09/178,060 filed Oct. 26, 1998, now U.S. Pat. No. 6,206,359 B1the prior application being incorporated herein by reference.

FIELD OF INVENTION

This invention relates generally to electrical stimulation therapy for neurologic and neuropsychiatric disorders, more specifically to neuromodulation therapy for depression, migraine, and neuropsychiatric disorders, as well as adjunct treatment for partial complex, generalized epilepsy and involuntary movement disorders utilizing an implanted lead-receiver and an external stimulator.

BACKGROUND

It has been observed clinically that electrical stimulation therapy for seizures produced mood improvement independent of the anti-seizure effects. This discovery led to medical research into the therapeutic effects of electrical stimulation for depression. Medical research has shown beneficial medical effects of vagus nerve stimulation (VNS) for severely depressed patients.

Vagus nerve stimulation, and the profound effects of electrical stimulation of the vagus nerve on central nervous system (CNS) activity, extends back to the 1930's. Medical studies in clinical neurobiology have advanced our understanding of anatomic and physiologic basis of the anti-depressive effects of vagus nerve stimulation.

Some of the somatic interventions for the treatment of depression include electroconvulsive therapy (ECT), tran-scranical magnetic stimulation, vagus nerve stimulation, and deep brain stimulation. The vagus nerve is the 10$^{th}$ cranial nerve, and is a direct extension of the brain. FIG. 1A, shows a diagram of the brain and spinal cord 24, with its relationship to the vagus nerve 54 and the nucleus tractus solitarius 14. FIG. 1B shows the relationship of the vagus nerve 54 with the other cranial nerves.

Vagus nerve stimulation is a means of directly affecting central function and is less invasive than deep brain stimulation (DBS). As shown in FIG. 1C, cranial nerves have both afferent pathway 19 (inward conducting nerve fibers which convey impulses toward the brain) and efferent pathway 21 (outward conducting nerve fibers which convey impulses to an effector). The vagus nerve is composed of 80% afferent sensory fibers carrying information to the brain from the head, neck, thorax, and abdomen. The sensory afferent cell bodies of the vagus reside in the nodose ganglion and relay information to the nucleus tractus solitarius (NTS) 14.

As shown schematically in FIGS. 1A and 1D, the nucleus of the solitary tract relays this incoming sensory information to the rest of the brain through three main pathways; (1) an autonomic feedback loop, (2) direct projection to the reticular formation in the medulla, and (3) ascending projections to the forebrain largely through the parabrachial nucleus (PBN) 20 and the locus ceruleus (LC) 22. The PBN 20 sits adjacent to the neucleus LC 22 (FIG. 1A). The PBN/LC 20/22 sends direct connections to every level of the forebrain, including the hypothalamus 26, and several thalamic 25 regions that control the insula and orbitofrontal 28 and prefontal cortices. Perhaps important for mood regulation, the PBN/LC 20/22 has direct connections to the amygdala 29 and the bed nucleus of the stria terminalis—structures that are implicated in emotion recognition and mood regulation.

In sum, incoming sensory (afferent) connections of the vagus nerve 54 provide direct projections to many of the brain regions implicated in nueropsychiatric disorders. These connections reveal how vagus nerve stimulation is a portal to the brainstem and connected regions. These circuits likely account for the neuropsychiatric effects of vagus nerve stimulation.

Increased activity of the vagus nerve is also associated with the release of more serotonin in the brain. Much of the pharmacologic therapy for treatment of migraines is aimed at increasing the levels of serotonin in the brain. Therefore, non-pharmacologic therapy of electrically stimulating the vagus nerve would have benefits for adjunct treatment of migraines and other ailments, such as obsessive compulsive disorders, that would benefit from increasing the level of serotonin in the brain.

The vagus nerve provides an easily accessible, peripheral route to modulate central nervous system (CNS) function. Other cranial nerves can be used for the same purpose, but the vagus nerve is preferred because of its easy accessibility. In the human body there are two vagal nerves (VN), the right VN and the left VN. Each vagus nerve is encased in the carotid sheath along with the carotid artery and jugular vein. The innervation of the right and left vagal nerves is different. The innervation of the right vagus nerve is such that stimulating it results in profound bradycardia (slowing of the heart rate). The left vagal nerve has some innervation to the heart, but mostly innervates the visceral organs such as the gastrointestinal tract. It is known that stimulation of the left vagal nerve does not cause any significant deleterious side effects.

Complex partial seizure is a common form of epilepsy, and some 30–40% of patients afflicted with this disorder are not well controlled by medications. Some patients have epileptogenic foci that may be identified and resected; however, many patients remain who have medically resistant seizures not amenable to resective surgery. Stimulation of the vagus nerve has been shown to reduce or abort seizures in experimental models. Early clinical trials have suggested that vagus nerve stimulation has beneficial effects for complex partial seizures and generalized epilepsy in humans. In addition, intermittent vagal stimulation has been relatively safe and well tolerated during the follow-up period available in these groups of patients. The minimal side effects of tingling sensations and brief voice abnormalities have not been distressing.

Most nerves in the human body are composed of thousands of fibers, of different sizes designated by groups A, B and C, which carry signals to and from the brain. The vagus nerve, for example, may have approximately 100,000 fibers of the three different types, each carrying signals. Each axon (fiber) of that nerve conducts only in one direction, in normal circumstances. The A and B fibers are myelinated (i.e., have a myelin sheath, constituting a substance largely composed of fat), whereas the C fibers are unmyelinated.

A commonly used nomenclature for peripheral nerve fibers, using Roman and Greek letters, is given in the table below,

| Group | External Diameter (μm) | Conduction Velocity (m/sec) |
| --- | --- | --- |
| Myelinated Fibers | | |
| Aα or IA | 12–20 | 70–120 |
| Aβ: IB | 10–15 | 60–80 |
| II | 5–15 | 30–80 |
| Aγ | 3–8 | 15–40 |
| Aδ or III | 3–8 | 10–30 |
| B | 1–3 | 5–15 |
| Unmyelinted fibers | | |
| C or IV | 0.2–1.5 | 0.5–2.5 |

The diameters of group A and group B fibers include the thicknesses of the myelin sheaths. Group A is further subdivided into alpha, beta, gamma, and delta fibers in decreasing order of size. There is some overlapping of the diameters of the A, B, and C groups because physiological properties, especially the form of the action potential, are taken into consideration when defining the groups. The smallest fibers (group C) are unmyelinated and have the slowest conduction rate, whereas the myelinted fibers of group B and group A exhibit rates of conduction that progressively increase with diameter. Group B fibers are not present in the nerves of the limbs; they occur in white rami and some cranial nerves.

Compared to unmyelinated fibers, myelinated fibers are typically larger, conduct faster, have very low stimulation thresholds, and exhibit a particular strength-duration curve or respond to a specific pulse width versus amplitude for stimulation. The A and B fibers can be stimulated with relatively narrow pulse widths, from 50 to 200 microseconds (μs), for example. The A fiber conducts slightly faster than the B fiber and has a slightly lower threshold. The C fibers are very small, conduct electrical signals very slowly, and have high stimulation thresholds typically requiring a wider pulse width (300–1,000 μs) and a higher amplitude for activation. Selective stimulation of only A and B fibers is readily accomplished. The requirement of a larger and wider pulse to stimulate the C fibers, however, makes selective stimulation of only C fibers, to the exclusion of the A and B fibers, virtually unachievable inasmuch as the large signal will tend to activate the A and B fibers to some extent as well.

The vagus nerve is composed of somatic and visceral afferents (i.e., inward conducting nerve fibers which convey impulses toward the brain) and efferents (i.e., outward conducting nerve fibers which convey impulses to an effector). Usually, nerve stimulation activates signals in both directions (bi-directionally). It is possible, however, through the use of special electrodes and waveforms, to selectively stimulate a nerve in one direction only (unidirectionally). The vast majority of vagal nerve fibers are C fibers, and a majority are visceral afferents having cell bodies lying in masses or ganglia in the skull. The central projections terminate largely in the nucleus of the solitary tract which sends fibers to various regions of the brain (e.g., the hypothalamus, thalamus, and amygdala).

The basic premise of vagal nerve stimulation for control of seizures is that vagal visceral afferents have a diffuse central nervous system (CNS) projection, and activation of these pathways has a widespread effect on neuronal excitability.

The cervical component of the vagus nerve ($10^{th}$ cranial nerve) transmits primarily sensory information that is important in the regulation of autonomic activity by the parasympathetic system. General visceral afferents constitute approximately 80% of the fibers of the nerve, and thus it is not surprising that vagal nerve stimulation (VNS) can profoundly affect CNS activity. With cell bodies in the nodose ganglion, these afferents originate from receptors in the heart, aorta, lungs, and gastrointestinal system and project primarily to the nucleus of the solitary tract which extends throughout the length of the medulla oblongata. A small number of fibers pass directly to the spinal trigeminal nucleus and the reticular formation.

As might be predicted from the electrophysiologic studies, the nucleus of the solitary tract has widespread projection to cerebral cortex, basal forebrain, thalamus, hypothalamus, amygdala, hippocampus, dorsal raphe, and cerebellum as shown in FIG. 1D (from *Epilepsia*, vol. 3, suppl.2: 1990, page S2).

Even though observations on the profound effect of electrical stimulation of the vagus nerve on central nervous system (CNS) activity, extends back to the 1930's, in the mid-1980s it was suggested that electrical stimulation of the vagus nerve might be effective in preventing seizures. Early studies on the effects of vagal nerve stimulation (VNS) on brain function focused on acute changes in the cortical electroencephalogram (EEG) of anesthetized animals. Investigators found that VNS could temporarily synchronize or desynchronize the electroencephalogram, depending on the level of anesthesia and the frequency or intensity of the vagal stimulus. These observations had suggested that VNS exerted its anticonvulsant effect by desynchronizing cortical electrical activity. However, subsequent clinical investigations have not shown VNS-induced changes in the background EEGs of humans. A study, which used awake and freely moving animals, also showed no VNS-induced changes in background EEG activity. Taken together, the findings from animal study and recent human studies indicate that acute desynchronization of EEG activity is not a prominent feature of VNS when it is administered during physiologic wakefulness and sleep, and does not explain the anticonvulsant effect of VNS.

The mechanism by which vagal nerve stimulation (VNS) exerts its influence on seizures is not entirely understood. An early hypotheses had suggested that VNS utilizes the relatively specific projection from the nucleus of the solitary track to limbic structures to inhibit partial seizures, particularly those involving cortex, which regulates autonomic activity or visceral sensations such as in temporal lobe epilepsy. Afferent VNS at the onset of a partial seizure could abort the seizure in the same way somatosensory stimuli can abort a seizure from the rolandic cortex; however, chronic intermittent stimulation may also produce an alteration in limbic circuitry that outlasts the stimulus and decreases epileptogenesis or limits seizure spread. Support for this hypothesis comes from studies of fos immunoreactivity in the brain of rats in response to VNS. Fos is a nuclear protein resulting from expression of early immediate genes in highly active neurons. VNS causes a specific fos immunolabeling in amygdala and limbic neocortex, suggesting that the antiepileptic effect may be mediated in these areas. Such activation of genetic mechanisms could account for the apparent sustained antiepileptic effect of intermittent stimulation.

Another possible mechanism that is being explored to explain an antiseizure effect of VNS is activation of the brainstem noradrenergic nuclei, lucus ceruleus and A5, which also show fos immunolabeling. Noradrenergic mechanisms are well known to influence seizure activity in genetic epilepsy-prone rats, and the anticonvulsant effects of VNS against maximal electroshock seizures can be blocked inactivation of the loc. ceruleus. Woodbury and Woodbury (1990) suggested that VS acts through increasing release of glycine or GABA since seizures induced by both PTZ and strychnine can be blocked by VNS. Other neruotransmitter systems may also be implicated since VNS increases cerebrospinal fluid homovanilic acid and 5-hydroxyindoleacetate, suggesting modulation of dopaminergic and serotonergic systems. Finally, a nonspecific alteration of activity in the brainstem reticular system with subsequent arousal must be considered.

VNS appears to have similar efficacy in both partial and generalized seizures in experimental models and in human epilepsy consistent with a nonspecific effect. Furthermore, the same inhibition of interictal corticalspike activity as seen with VNS occurs in animals during electrical stimulation of the midbrain reticular formation or with thermal stimulation of somatosensory nerves in the rat tail. Reduction of experimental generalized spike wave by arousal has also been documented. Similarly, nonspecific afferent stimulation has been well demonstrated in humans to suppress focal spikes, generalized spike waves, and seizures.

VNS may inhibit seizures directly at the level of cerebral cortical neuronal irritability, or at the level of diffuse ascending subcortical projection systems, or both. Thus, VNS is also well suited for the treatment of medication-resistant symptomatic generalized epilepsy (SGE), in which, characteristically both focal and generalized features are found on interictal EEGs and also in clinical seizure types.

One type of prior non-pharmacological therapy for depression, migraines, neuropsychiatric disorders, and epilepsy is generally directed to the use of an implantable lead and an implantable pulse generator technology or "cardiac pacemaker-like" technology. In these applications, the pulse generator is programmed via a personnel computer (PC) based programmer that is modified and adapted with a programmer wand which is placed on top of the skin over the pulse generator implant site. Each parameter is programmed independent of the other parameters. Therefore, millions of different combinations of programs are possible. In the instant patent, preferably approximately nine programs are pre-selected.

U.S. Pat. No. 3,796,221 (Hagfors) is directed to controlling the amplitude, duration and frequency of electrical stimulation applied from an externally located transmitter to an implanted receiver by inductively coupling. Electrical circuitry is schematically illustrated for compensating for the variability in the amplitude of the electrical signal available to the receiver because of the shifting of the relative positions of the transmitter-receiver pair. By highlighting the difficulty of delivering consistent pulses, this patent points away from applications such as the current application, where consistent therapy needs to be continuously sustained over a prolonged period of time (24 hours a day for years). The methodology disclosed is focused on circuitry within the receiver, which would not be sufficient when the transmitting coil and receiving coil assume significantly different orientation, which is likely in the current application. The present invention discloses a novel approach for this problem.

U.S. Pat. No. 5,304,206 (Baker, Jr. et al) is directed to activation techniques for implanted medical stimulators. The system uses either a magnet to activate the reed switch in the device, or tapping which acts through the piezoelectric sensor mounted on the case of the implanted device, or a combination of magnet and tapping sequence.

U.S. Pat. Nos. 4,702,254, 4,867,164 and 5,025,807 (Zabara) generally disclose animal research and experimentation related to epilepsy and the like and are directed to stimulating the vagus nerve by using pacemaker technology, such as an implantable pulse generator. These patents are based on several key hypotheses, some of which have since been shown to be incorrect. The pacemaker technology concept consists of a stimulating lead connected to a pulse generator (containing the circuitry and DC power source) implanted subcutaneously or submuscularly, somewhere in the pectoral or axillary region, with an external personal computer (PC) based programmer. Once the pulse generator is programmed for the patient, the fully functional circuitry and power source are fully implanted within the patient's body. In such a system, when the battery is depleted, a surgical procedure is required to disconnect and replace the entire pulse generator (circuitry and power source). These patents neither anticipate practical problems of an inductively coupled system for adjunct therapy of epilepsy, nor suggest solutions to the same for an inductively coupled system for adjunct therapy of partial complex or generalized epilepsy. FIG. 4 in all three above Zabara patents show the stimulation electrode around the right vagus nerve. It is well known that stimulation of right vagus can lead to profound bradycardia (slowing of the heart rate), an unwanted complication.

U.S. Pat. No. 5,299,569 (Wernicke et al.) is directed to the use of implantable pulse generator technology for treating and controlling neuropsychiatric disorders including schizophrenia, depression, and borderline personality disorder.

U.S. Pat. No. 5,752,979 (Benabid) is directed to a method of controlling epilepsy with stimulation directly into the brain, utilizing an implantable generator. More specifically, Benabid discloses electrically stimulating the external segment of the globus palliaus nucleus of the brain causing increased excitation, thereby increasing inhibition of neural activity in the subthalamic nucleus and reducing excitatory input to the substantia nigra leading to a reduction in the occurrence of seizures.

U.S. Pat. No. 5,540,734 (Zabara) is directed to stimulation of one or both of a patient's trigeminal and glossopharyngeal nerve utilizing an implanted pulse generator.

U.S. Pat. No. 5,031,618 (Mullett) discloses a position sensor for chronically implanted neuro stimulator for stimulating the spinal cord. The position sensor, located in a chronically implanted programmable spinal cord stimulator, modulates the stimulation signals depending on whether the patient is erect or supine.

U.S. Pat. No. 4,573,481 (Bullara) is directed to an implantable helical electrode assembly configured to fit around a nerve. The individual flexible ribbon electrodes are each partially embedded in a portion of the peripheral surface of a helically formed dielectric support matrix.

U.S. Pat. No. 3,760,812 (Timm et al.) discloses nerve stimulation electrodes that include a pair of parallel spaced apart helically wound conductors maintained in this configuration.

U.S. Pat. No. 4,979,511 (Terry) discloses a flexible, helical electrode structure with an improved connector for attaching the lead wires to the nerve bundle to minimize damage.

An implantable pulse generator and lead with a PC based external programmer is advantageous for cardiac pacing applications for several reasons, including:

1) A cardiac pacemaker must sense the intrinsic activity of the heart, because cardiac pacemakers deliver electrical output primarily during the brief periods when patients either have pauses in their intrinsic cardiac activity or during those periods of time when the heart rate drops (bradycardia) below a certain pre-programmed level. Therefore, for most of the time, in majority of patients, the cardiac pacemaker "sits" quietly monitoring the patient's intrinsic cardiac activity.

2) The stimulation frequency for cardiac pacing is typically close to 1 Hz, as opposed to approximately 20 Hz or higher, typically used in nerve stimulation applications.

3) Patients who require cardiac pacemaker support are typically in their 60's, 70's or 80's years of age.

The combined effect of these three factors is that the battery in a pacemaker can have a life of 10–15 years. Most patients in whom a pacemaker is indicated are implanted only once, with perhaps one surgical pulse generator replacement.

In contrast, patients with partial complex epilepsy or generalized epilepsy in whom electrical stimulation is beneficial are much younger as a group, typically ranging from 12 to 45 years in age. Also, stimulation frequency is typically 20 Hz or higher, and the total stimulation time per day is much longer than for cardiac pacemakers. As a result, battery drain is typically much higher for nerve stimulation applications than for cardiac pacemakers.

The net result of these factors is that the battery will not last nearly as long as in cardiac pacemakers. Because the indicated patient population is also much younger, the expense and impact of surgical generator replacement will become significant, and detract from the appeal of this therapy. In fact, it has been reported in the medical literature that the battery life can be as short as one and half years for implantable nerve stimulator. (R. S. McLachlan, p. 233).

There are several other advantages of the present inductively coupled system.

1) The hardware components implanted in the body are much less. This is advantageous for the patient in terms of patient comfort, and it decreases the chances of the hardware getting infected in the body. Typically, when an implantable system gets infected in the body, it cannot be easily treated with antibiotics and eventually the whole implanted system has to be explanted.

2) Because the power source is external, the physician can use stimulation sequences that are more effective and more demanding on the power supply, such as longer "on" time.

3) With the controlling circuitry being external, the physician and the patient may easily select from a number of predetermined programs, override a program, manually operate the device or even modify the predetermined programs.

4) The external inductively-coupled nerve stimulation (EINS) system is quicker and easier to implant.

5) The external pulse generator does not need to be monitored for "End-of-Life" (EOL) like the implantable system, thus resulting in cost saving and convenience.

6) The EINS system can be manufactured at a significantly lower cost of an implantable pulse generator and programmer system, providing the patient and medical establishment with cost effective therapies.

7) The EINS system makes it more convenient for the patient or caretaker to turn the device on during an "Aura" that sometimes precedes the seizures. Also, because programming the device is much simpler, the patient or caretaker may reprogram the device at night time by simply pressing one or two buttons to improve patient comfort.

8) Occasionally, an individual responds adversely to an implanted medical device and the implanted hardware must be removed. In such a case, a patient having the EINS systems has less implanted hardware to be removed and the cost of the pulse generator does not become a factor.

In the conventional manner of implanting, a cervical incision is made above the clavicle, and another infraclavicular incision is made in the deltapectoral region for the implantable stimulus generator pocket. To tunnel the lead to the cervical incision, a shunt-passing tool is passed from the cervical incision to the generator pocket, where the electrode is attached to the shunt-passing tool and the electrode is then "pulled" back to the cervical incision for attachment to the nerve. This standard technique has the disadvantage that it is time consuming and it tends to create an open space in the subcutaneous tissue. Post surgically the body will fill up this space with serous fluid, which can be undesirable.

To make the subcutaneous tunneling simpler and to avoid possible complication, one form of the implantable lead body is designed with a hollow lumen to aid in implanting. In this embodiment, a special tunneling tool slides into a hollow lumen. After the cervical and infraclavicular incisions are made, the tunneling tool and lead are simply "pushed" to the cervical incision and the tunneling tool is pulled out. Since the tunneling tool is inside the lead, no extra subcutaneous space is created around the lead, as the lead is pushed. This promotes better healing post-surgically.

The apparatus and methods disclosed herein also may be appropriate for the treatment of other conditions, as disclosed in co-pending applications filed on Oct. 26, 1998, entitled APPARATUS AND METHOD FOR ADJUNCT (ADD-ON) THERAPY OF DEMENTIA AND ALZHEIMER'S DISEASE UTILIZING AN IMPLANTABLE LEAD AND AN EXTERNAL STIMULATOR and APPARATUS AND METHOD FOR ADJUNCT (ADD-ON) THERAPY FOR PAIN SYNDROMES UTILIZING AN IMPLANTABLE LEAD AND AN EXTERNAL STIMULATOR, the disclosures of which are incorporated herein by reference.

SUMMARY OF THE INVENTION

The apparatus and methodology of this invention generally relates to the adjunct (add-on) treatment of depression, migraine, neuropsychiatric disorders, partial complex epilepsy, generalized epilepsy, and involuntary movement disorders such as in Parkinson's disease. More particularly, the apparatus and methodology in accordance with the invention provides a more adaptable and less intrusive treatment for such conditions. In one embodiment of the invention, the apparatus consists of an easy to implant lead-receiver, an external stimulator containing controlling circuitry and power supply, and an electrode containing a coil for inductively coupling the external pulse generator to the implanted lead-receiver. A separately provided tunneling tool may be used as an aid for implanting the lead-receiver.

In another embodiment of the invention, the external stimulator has two modes of operation: one with several pre-determined programs that may be selectively locked-out by the manufacturer or physician and another with a manual override.

In another embodiment of the invention, the implantable lead-receiver is inductively coupled to the external stimulator via a patch electrode containing coil. One feature of this invention is to consistently deliver energy from an external coil to an internal coil in an ambulatory patient. A design of the external patch contains means for compensating for relative movement of the axis of the external and internal coils by deflecting the energy via targets located in the external patch.

Another feature of this invention is to provide an apparatus to aid in implanting the lead-receiver, including a hollow lumen in the lead body to receive a tunneling tool.

BRIEF DESCRIPTION OF THE DRAWINGS

For the purpose of illustrating the invention, there are shown in accompanying drawing forms which are presently preferred, it being understood that the invention is not intended to be limited to the precise arrangement and instrumentalities shown.

FIG. 10 is a diagram of a tunneling tool for aiding in the implantation of the lead-receiver.

FIG. 11 is diagram of another tunneling tool for aiding in the implantation of the lead-receiver.

FIG. 15 is a diagram of a hydrogel electrode.

FIG. 16 is a diagram of a lead-receiver utilizing a fiber electrode at the distal end.

FIG. 21 is a diagram of an electrode containing steroid drug in a silicone collar at the base of electrode.

FIG. 22 is a diagram of an electrode with steroid drug coated on the surface of the electrode.

FIG. 23 is a diagram of cross sections of implantable lead-receiver body showing different lumens.

Figure 1A:
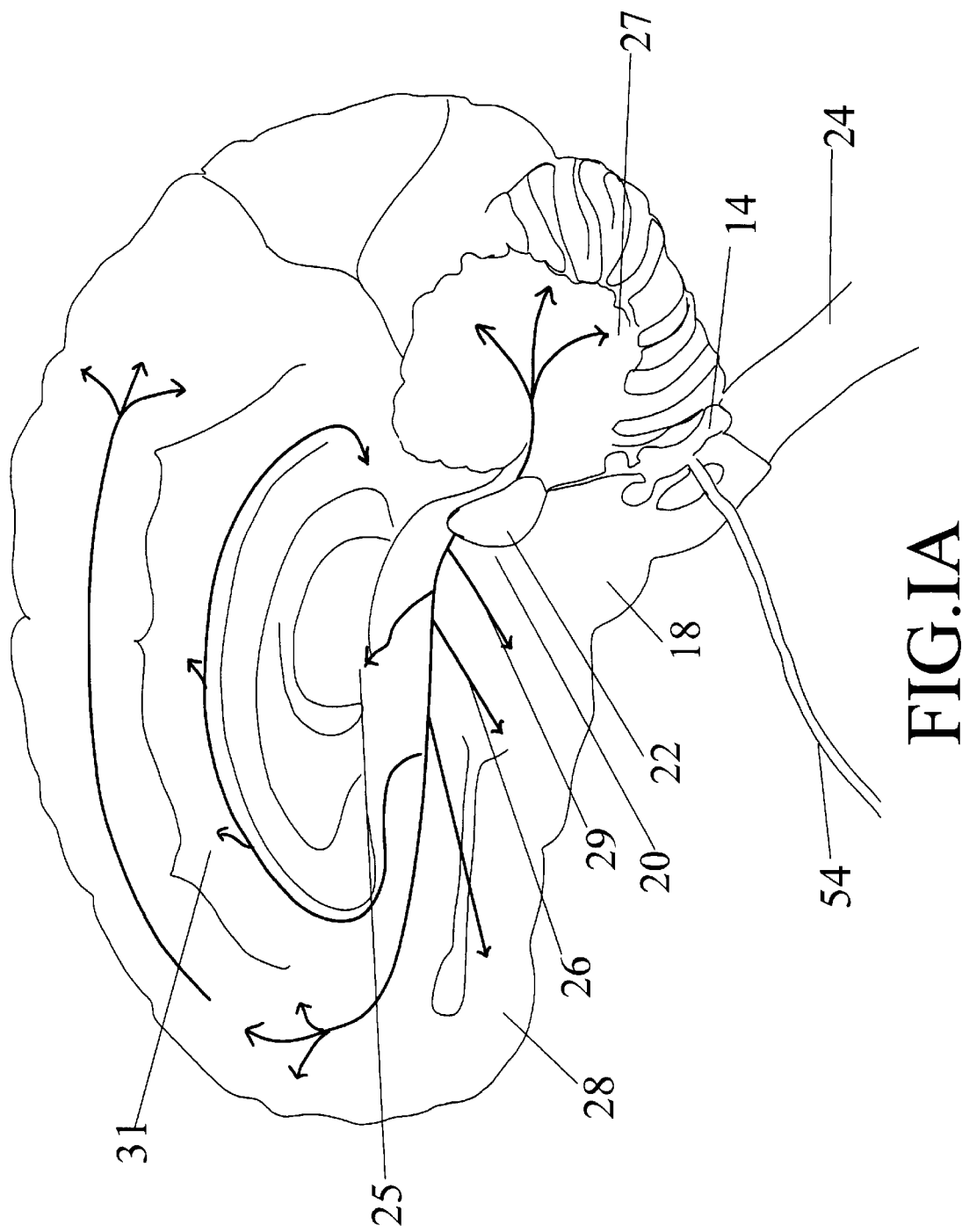
FIG. 1A is a diagram of the lateral view of brain and spinal cord, with its relationship to the vagus nerve.
Figure 1B:
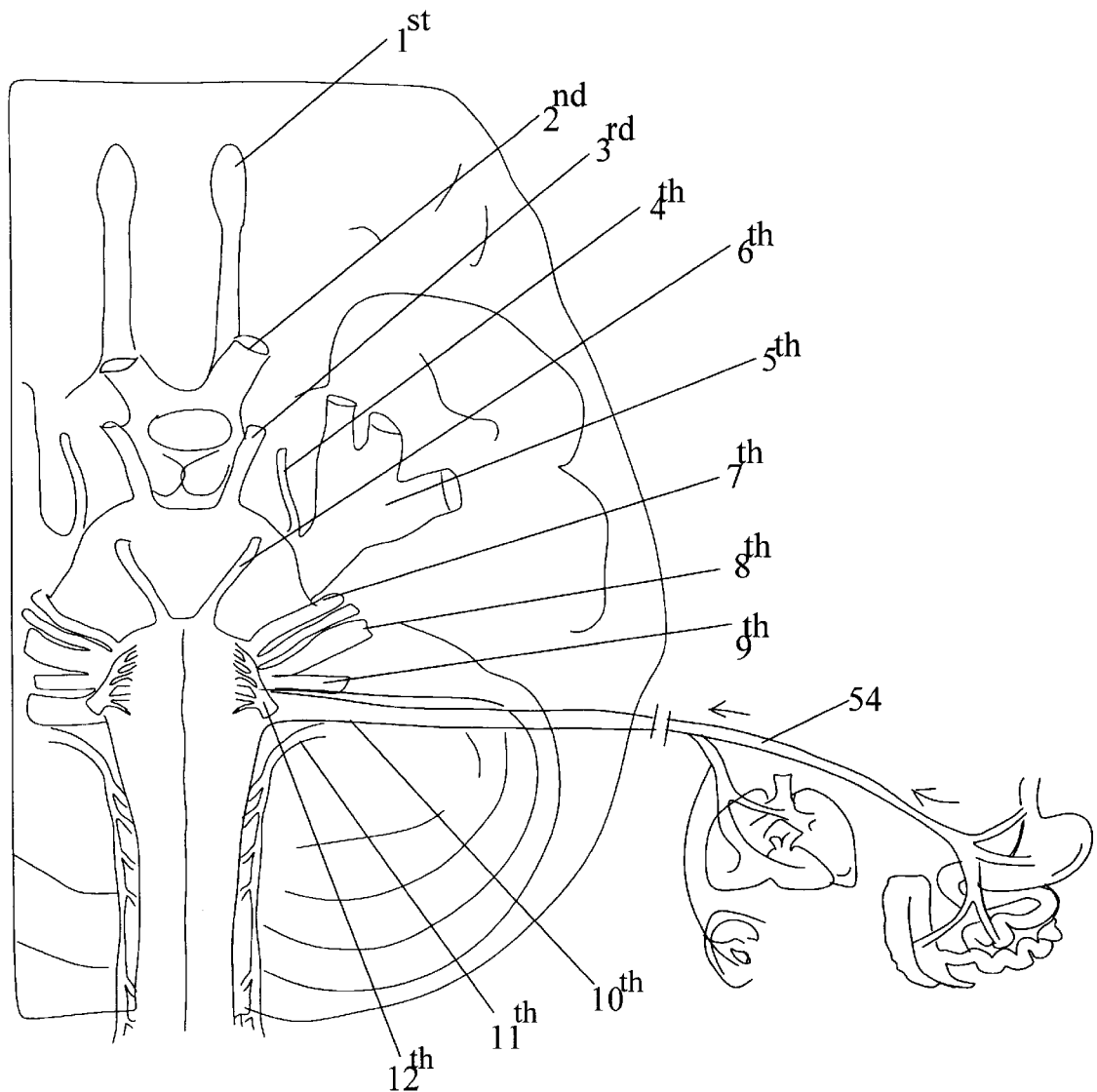
FIG. 1B is a diagram of the base of brain showing the relationship of vagus nerve to the other cranial nerves.
Figure 1C:
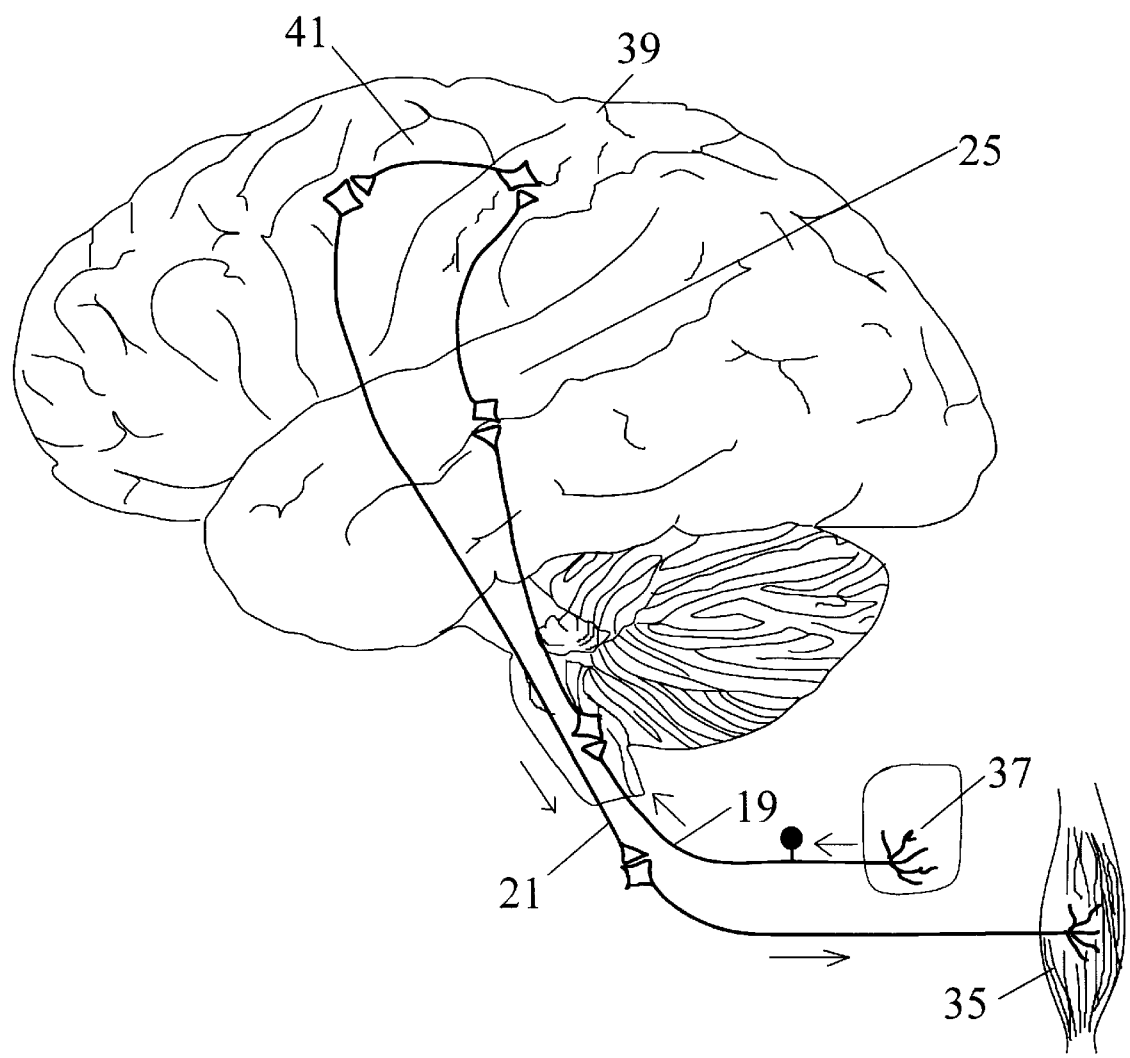
FIG. 1C is a diagram of brain showing afferent and efferent pathways.
Figure 1D:
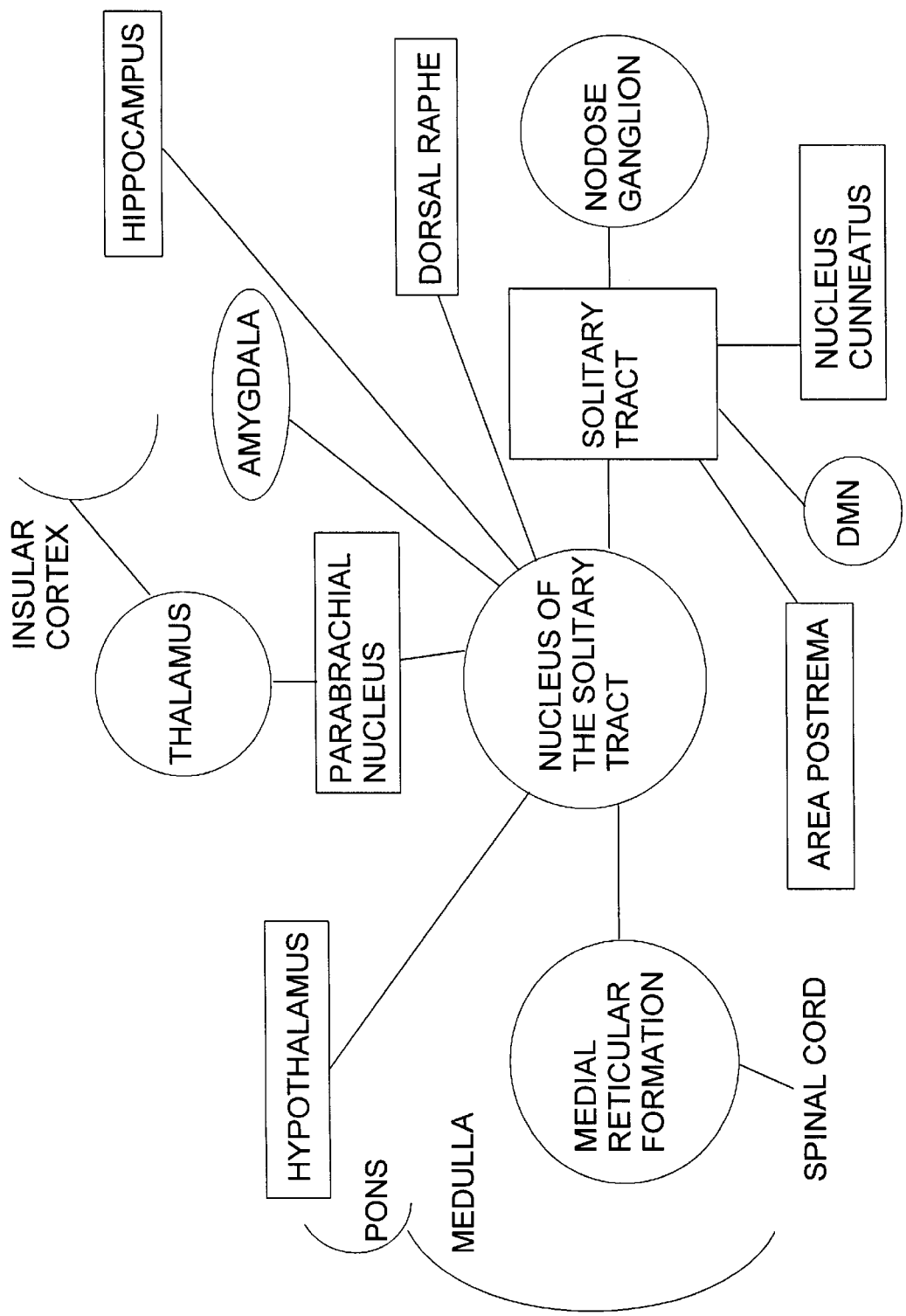
FIG. 1D is diagram of vagal nerve afferents through the nucleus of the solitary tract.

The following are reference numbers in the drawings:

1. olfactory nerve
2. optic nerve
3. oculomotor nerve
4. trochlear nerve
5. trigeminal nerve
6. abducens nerve
7. facial nerve
8. acoustic nerve
9. glossopharyngeal nerve
11. accessory nerve
12. hypoglosal nerve
14. nucleus tractus solitaris
15. parabrachial nucleus (PB)
17. nucleus locus coeruleus
18. pons
19. afferent pathway
20. parabrachial nucleus (PB)
21. efferent pathway
22. nucleus locus coeruleus (LC)
24. spinal cord
25. thalamus
26. hypothalamus
27. corebellum
28. orbito-frontal cortex
29. amygdala
31. cingulate gyrus
32. patient
34. implantable lead-receiver
35. muscle
36. coil-end of the external patch
37. skin receptors
38. wire of external patch
39. primary somatic sensory cortex
40. terminal end of the external patch
41. primary motor cortex
42. external stimulator
43. external patch electrode
44. belt of external stimulator
45. ferrite target
46. outer (transmitting primary) coil
48. inner (receiving secondary) coil
49. proximal end of lead-receiver
50. adhesive portion of external patch electrode
51. driving voltage of transmitter coil
52. distal ball electrode
53. zero voltage of receiver coil
54. vagus nerve
55. signal voltage across receiver coil 56. carotid artery
57. ferrite targets in external patch
58. jugular vein
59. body of lead-receiver
60. working lumen of lead-receiver body
62. hollow lumen of lead-receiver body
64. schematic of lead-receiver circuitry
65. cable connecting cathode and anode
68. tuning capacitor in electrical schematic and in hybrid
69. selector
70. zenor diode
71. pre-determined programs in block diagram
72. capacitor used in filtering
73. patient override in block diagram
74. resister used in filtering
75. programmable control logic in block diagram
76. capacitor to block DC component to distal electrode
77. programming station in block diagram
78. case of lead-receiver
79. pulse frequency oscillator in block diagram
80. distal electrode in schematic of lead-receiver
81. battery (DC) in block diagram
82. working lumen in a cross section
83. amplifier in block diagram
84. hollow lumen in a cross-section
85. indicator in block diagram
86. small handle of alternate tunneling tool
87. low pass filter in block diagram
88. big handle of the tunneling tool
89. antenna in block diagram
90. skin
91. metal rod portion of the tunneling tool with big handle
92. punched holes in body of the lead receiver to promote fibrosis
93. metal rod portion of the alternative tunneling tool with small handle
94. alternative tunneling tool
95. tunneling tool with big handle
96. silicone covering proximal end
98. hybrid assembly
100. hydrogel
102. platinum electrodes around hydrogel
104. fiber electrode
105. spiral electrode
106. Dacron polyester or Polyimide
108. platinum fiber
110. exposed electrode portion of spiral electrode
112. polyurethane or silicone insulation in spiral electrode
114. "virtual" electrode
118. excitable tissue
120. non-excitable tissue
121. steroid plug inside an electrode
122. body of electrode
124. electrode tip
126. silicone collar containing steroid
128. steroid membrane coating
130. anchoring sleeve
132A–F lumens
134A–C larger hollow lumen for lead introduction

DESCRIPTION OF THE INVENTION

Figure 2A:
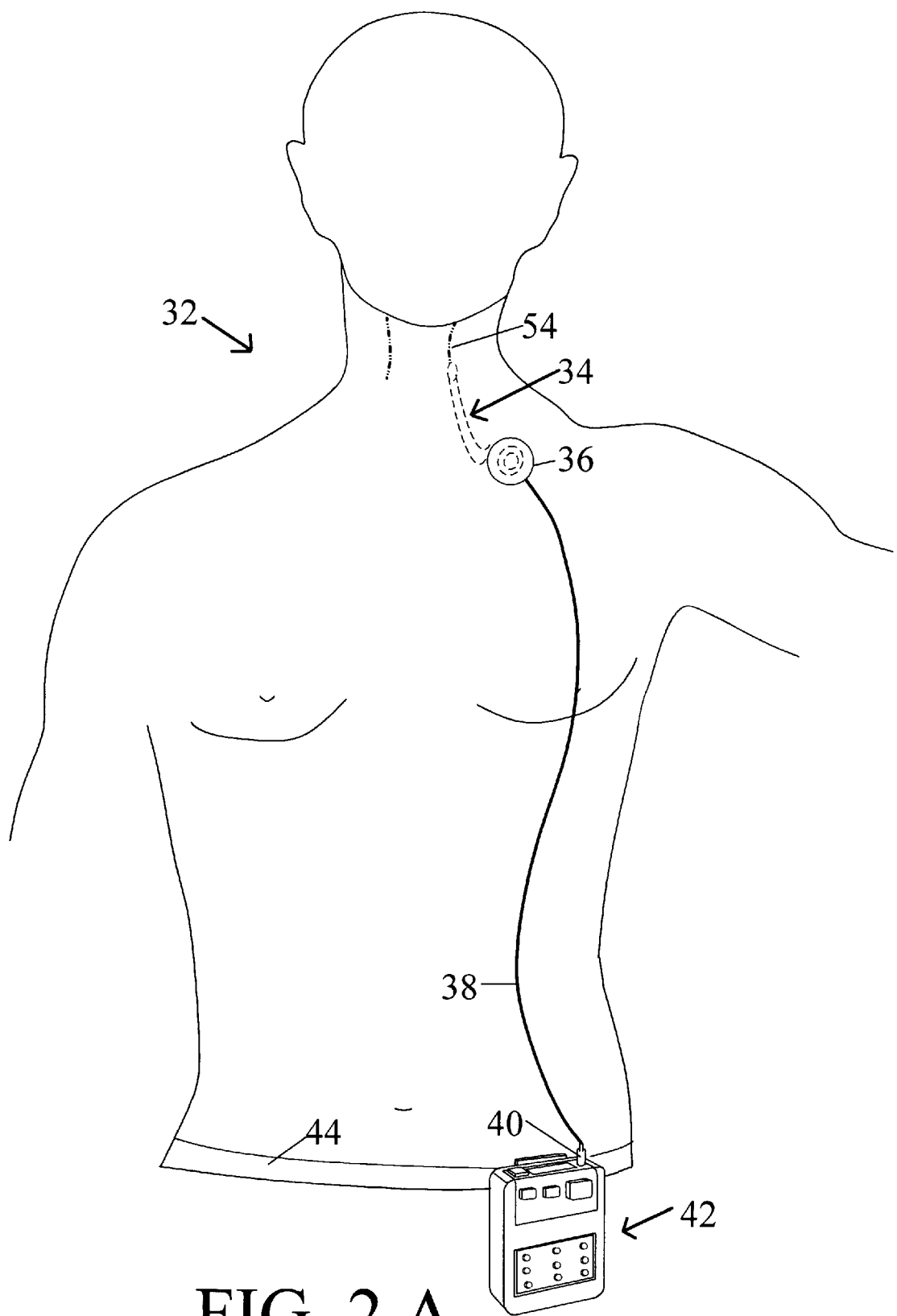
FIG. 2A is a diagram showing a patient wearing an external inductively-coupled nerve stimulator (EINS) system.
Figure 2:
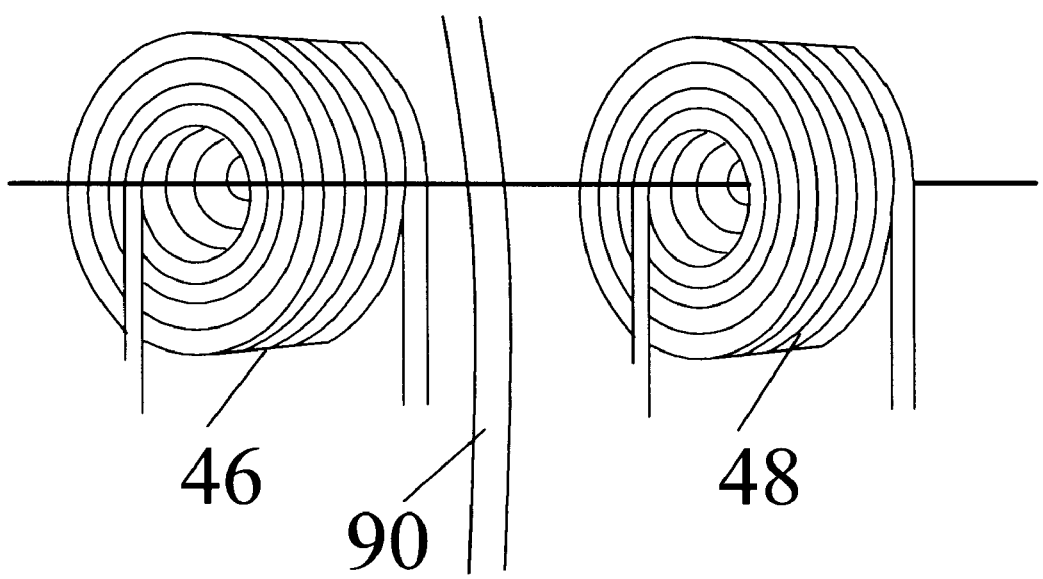
FIG. 2B is a diagram showing two coils along their axis, in a configuration such that the mutual inductance would be maximum.

FIG. 2A shows a schematic diagram of a patient 32 with an implantable lead-receiver 34 and an external stimulator 42, clipped on to a belt 44 in this case. The external stimulator 42, may alternatively be placed in a pocket or other carrying device. An external patch electrode 36 provides the coupling between the external stimulator 42 and the implantable lead-receiver 34.

Figure 5:
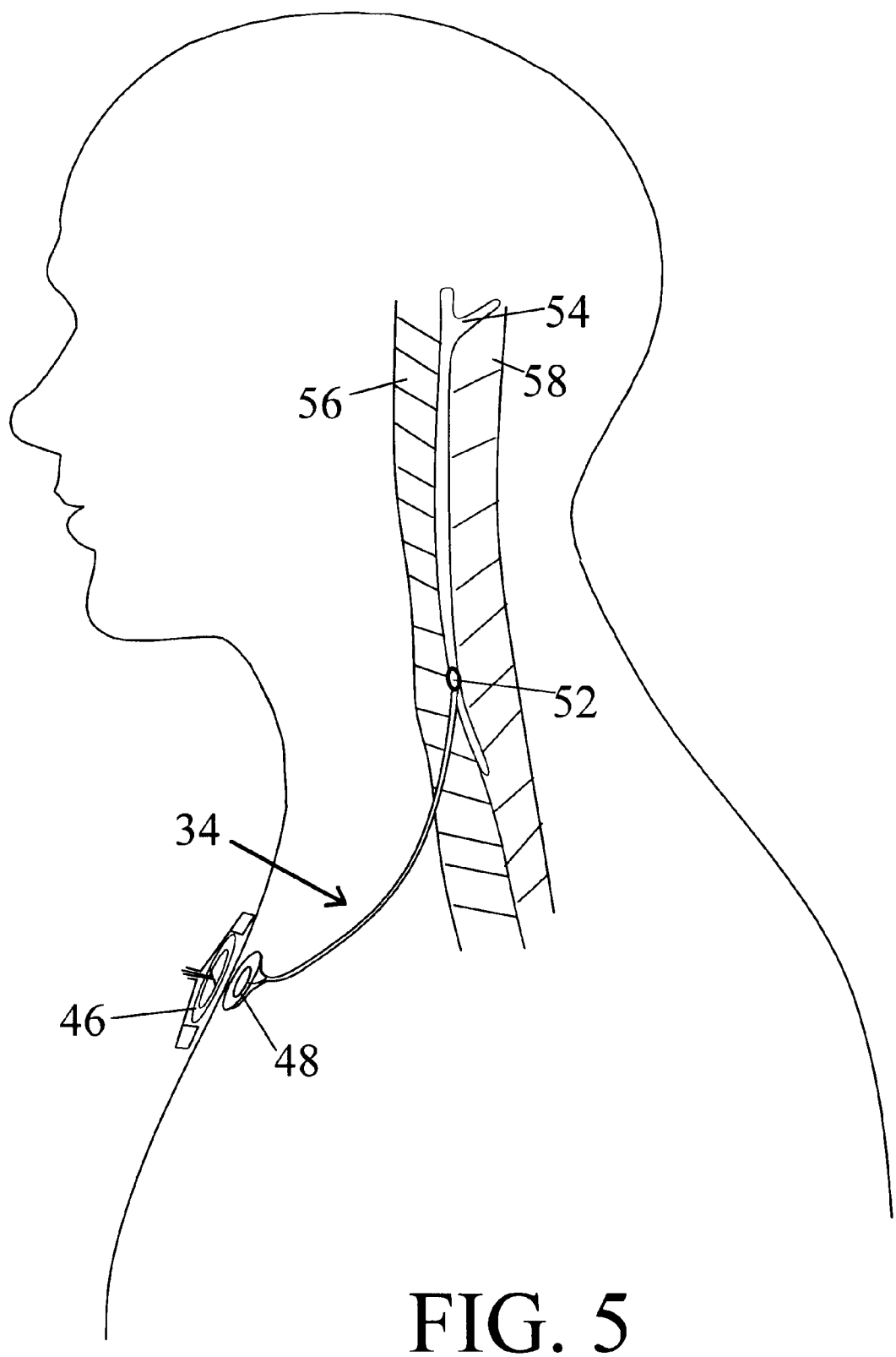
FIG. 5 is a diagram showing the implanted lead-receiver and the transmitting coil.

The external stimulator 42 is inductively coupled to the lead-receiver 34. As shown in FIG. 2B, when two coils are arranged with their axes on the same line, current sent through coil 46 creates a magnetic field that cuts coil 48 which is placed subcutaneously. Consequently, a voltage will be induced in coil 48 whenever the field strength of coil 46 is changing. This induced voltage is similar to the voltage of self-induction but since it appears in the second coil because of current flowing in the first, it is a mutual effect and results from the mutual inductance between the two coils. Since these two coils are coupled, the degree of coupling depends upon the physical spacing between the coils and how they are placed with respect to each other. Maximum coupling exists when they have a common axis and are as close together as possible. The coupling is least when the coils are far apart or are placed so their axes are at right angles. As shown in FIG. 5, the coil 48 inside the lead-receiver 34 is approximately along the same axis as the coil 46 in the external skin patch 36.

Figure 3A:
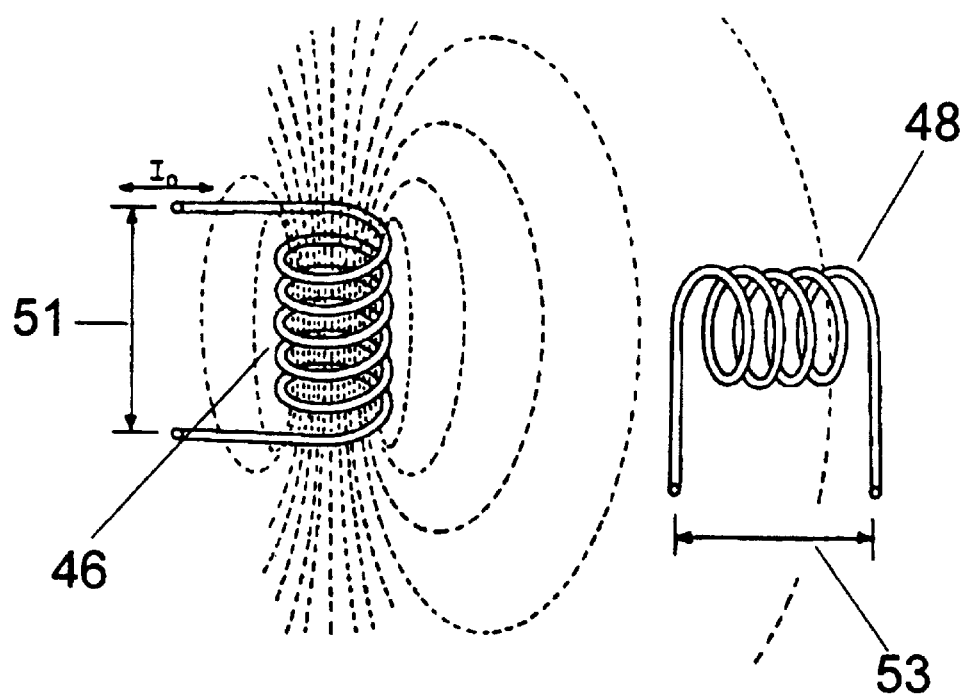
FIG. 3A is a diagram showing the effects of two coils with axes at right angles.
Figure 3B:
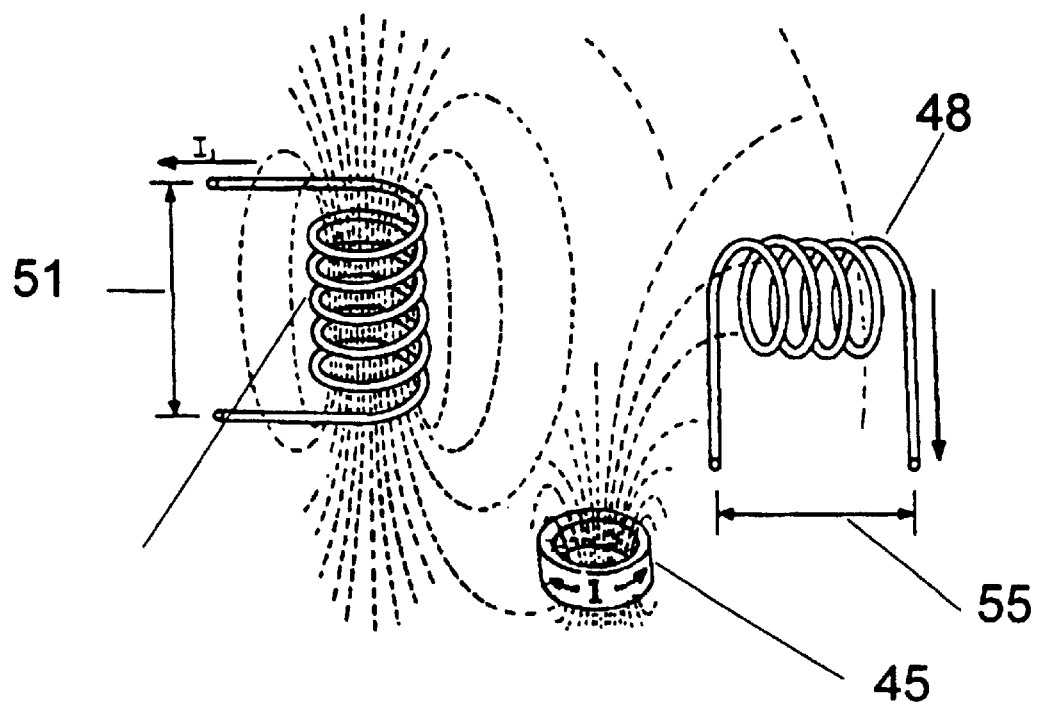
FIG. 3B is a diagram showing the effects of two coils with axes at right angles, with a ferrite target included.
Figure 4A:
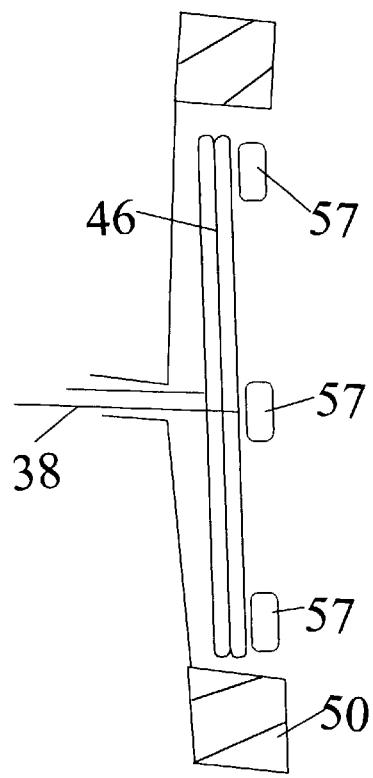
FIG. 4A is a side view of an external patch showing the transmitting coil and targets.
Figure 4B:
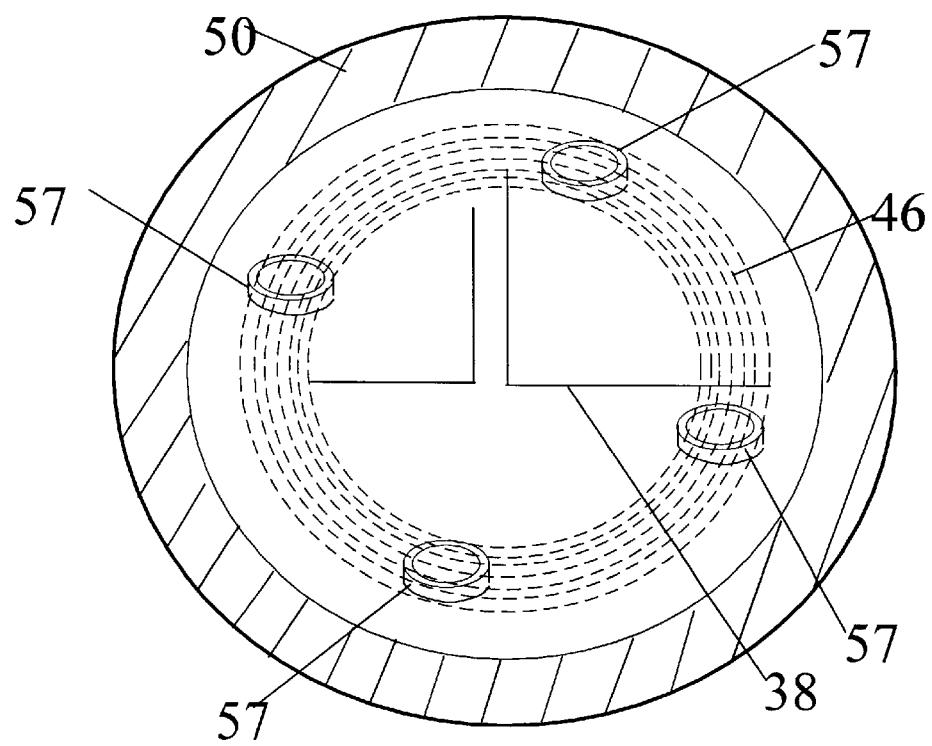
FIG. 4B is top view of an external patch showing the transmitting coil and targets.

As shown in FIG. 3A, when the axis of transmitting coil 46 is at right angles to the axis of the receiving coil 48, a given driving voltage 51 results in zero voltage 53 across the receiving coil 48. But, as shown in FIG. 3B by adding ferrite target 45, a given driving voltage 51 through the transmitting coil 46 results in a signal voltage 55 across the receiver coil 48. The efficiency is improved by having multiple ferrite targets. An alternate external patch shown in FIGS. 4A and 4B contains multiple targets 57. FIG. 4A shows a side view of the patch, and FIG. 4B shows a top view of the patch. Having multiple targets 57 in the external patch 43 compensates for non-alignment of the axis between the transmitting coil 46 and receiving coil 48. Since relative rotations between the axis of external transmitting coil 46 and internal receiving coil 48 which may occur during breathing, muscle contractions, or other artifacts are compensated for, results in continuous prolonged stimulation.

Figures 6, 7:
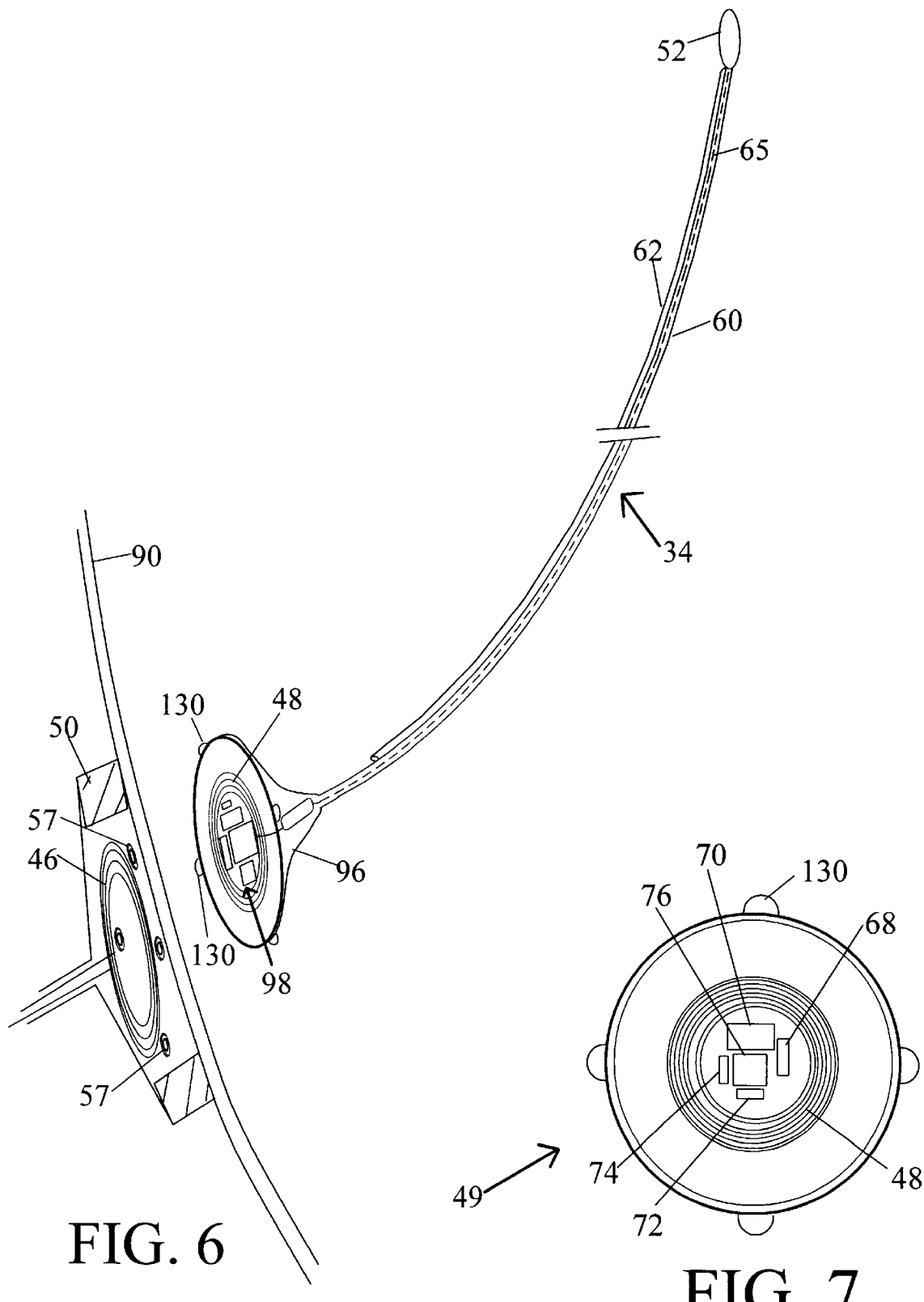
FIG. 6 is a diagram showing the implanted lead-receiver underneath the skin, also showing the relative position of the external coil.
FIG. 7 is a diagram showing the proximal end of the lead-receiver.
Figure 8:
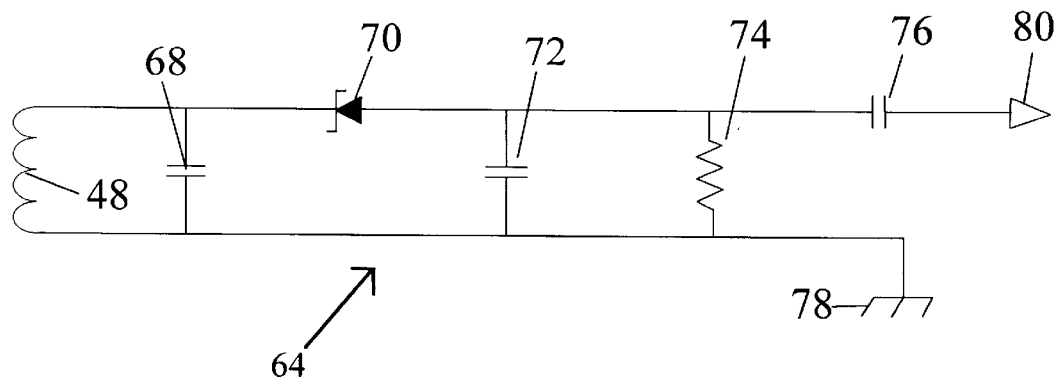
FIG. 8 is a diagram of circuitry within the proximal portion of the implanted lead-receiver.

Referring to FIG. 6, the implantable lead-receiver 34 looks somewhat like a golf "tee" and is the only implantable portion of the system. The "head" or proximal end 49 contains the coil 48 and electronic circuitry (hybrid) 98 which is hermetically sealed, and covered with silicone. It also has four anchoring sleeves 130 for tying it to subcutaneous tissue. FIG. 7 is a close-up view of the proximal portion 49 of the lead-receiver 34 containing the circuitry (hybrid) 98. This circuitry is shown schematically in FIG. 8. A coil 48 (preferably approximately 15 turns) is directly connected to the case 78. The external stimulator 42 and external patch 36 transmit the pulsed alternating magnetic field to receiver 64 whereat the stimulus pulses are detected by coil 48 and transmitted to the stimulus site (vagus nerve 54). When exposed to the magnetic field of transmitter 36, coil 48 converts the changing magnetic field into corresponding voltages with alternating polarity between the coil ends. A capacitor 68 is used to tune coil 48 to the high-frequency of the transmitter 36. The capacitor 68 increases the sensitivity and the selectivity of the receiver 64, which is made sensitive to frequencies near the resonant frequency of the tuned circuit and less sensitive to frequencies away from the resonant frequency. A zenor diode 70 in the current path is used for regulation and to allow the current that is produced by the alternating voltage of the coil to pass in one direction only. A capacitor 72 and resistor 74 filter-out the high-frequency component of the receiver signal and thereby leave a current of the same duration as the burst of the high-frequency signal. Capacitor 76 blocks any net direct current to the stimulating electrode tip 80, which is made of platinum/iridium (90%-10%).

Alternatively, the stimulating electrode can be made of platinum or platinum/iridium in ratio's such as 80% Platinum and 20% Iridium.

The circuit components are soldered in a conventional manner to an upper conductive layer on a printed circuit board. The case 78 is connected to the coil 48 and is made of titanium. The case 78 also serves as the return electrode (anode). The surface area of the anode exposed to the tissue is much greater than the surface area of the stimulating electrode 80 (cathode). Therefore, the current density at the anode is too low to unduly stimulate tissue that is in contact with the anode. Alternatively, a bipolar mode of stimulation can also be used. In the bipolar mode of stimulation the cathode and anode are in close proximity to each other.

The body of the lead-receiver 34 is made of medical grade silicone (available from NuSil Technology, Applied silicone or Dow Chemical). Alternatively, the lead body 59 may be made of medical grade polyurethane (PU) of 55D or higher durometer, such as available from Dow Chemical. Polyurethane is a stiffer material than silicone. Even though silicone is a softer material, which is favorable, it is also a weaker material than PU. Therefore, silicone coated with Teflon (PTFE) is preferred for this application. PTFE coating is available from Alpa Flex, Indianapolis, Indiana.

Figure 9:
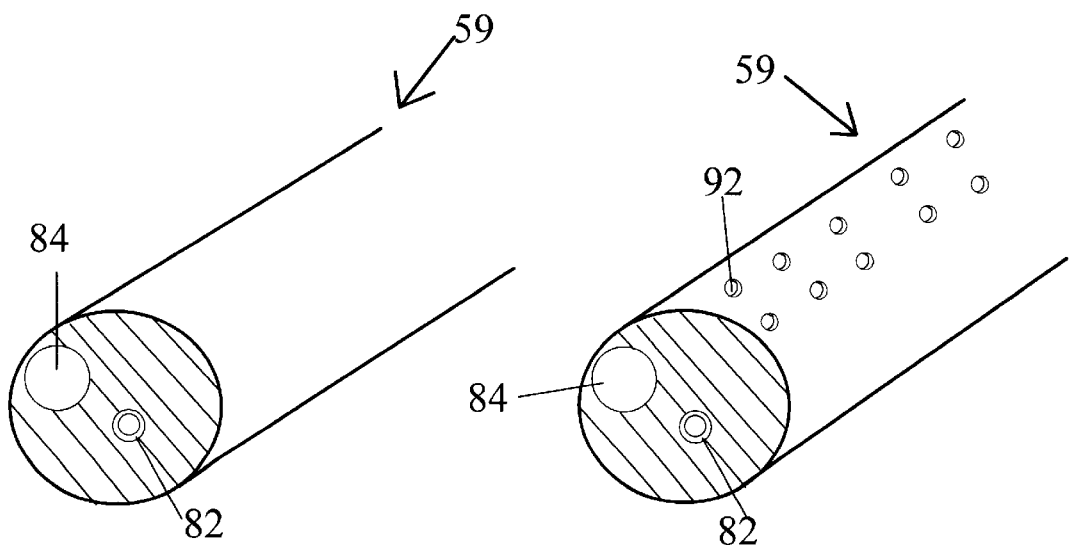
FIG. 9 is a diagram of the body of the lead-receiver.

FIG. 9 shows a close-up of the lead body 59 showing two lumens 82, 84. Lumen 82 is the "working" lumen, containing the cable conductor 65 which connects to the stimulating electrode 52. The other lumen 84 is preferably slightly larger and is for introducing and placing the lead in the body. Alternatively, lumen 84 may have small holes 92 punched along the length of the lead. These small holes 92 will promote fibrotic tissue in-growth to stabilize the lead position and inhibit the lead from migrating.

Silicone in general is not a very slippery material, having a high coefficient of friction. Therefore, a lubricious coating is added to the body of the lead. Such lubricous coating is available from Coating Technologies Inc. (Scotch Plains, N.J.). Since infection still remains a problem in a small percentage of patients, the lead may be coated with antimicrobial coating such as Silver Sulfer Dizene available from STS Biopolymers, Henrietta, N.Y. The lead may also be coated with anti-inflammatory coating.

The distal ball electrode 52, shown in FIG. 6 is made of platinum/iridium (90% platinum and 10% iridium). Platinum/iridium electrodes have a long history in cardiac pacing applications. During the distal assembly procedure, the silicone lead body 59 is first cleaned with alcohol. The conductor cable 65 (available from Lake Region, Minn.) is passed through the "working" lumen 82. The cable is inserted into the distal electrode 52, and part of the body of electrode is crimped to the cable 65 with a crimper. Alternatively, the cable conductor 65 may be arc welded or laser welded to the distal electrode 52. The distal end of the insulation is then slided over the crimp such that only the tissue stimulating portion of the distal electrode 52 is exposed. Following this, a small needle is attached to a syringe filled with medical glue. The needle is inserted into the distal end of insulation, and small amounts of medical glue are injected between the distal end of the insulation and distal electrode 52. The assembly is then cured in an oven.

As shown in FIGS. 9 and 10, a tunneling tool 95 is inserted into the empty lumen 84 to push the distal end (containing the cathode electrode 52) towards the vagus nerve 54. The tunneling tool 95, is comprised of a metal rod 91 and a handle 88. As shown in FIG. 11, another tunneling tool 94 with a smaller handle 86 may also be used. Both are available from Popper and Sons, New Hyde Park, N.Y. or Needle Technology. Alternatively, the tunneling tool may be made of strong plastic or other suitable material.

Figure 12:
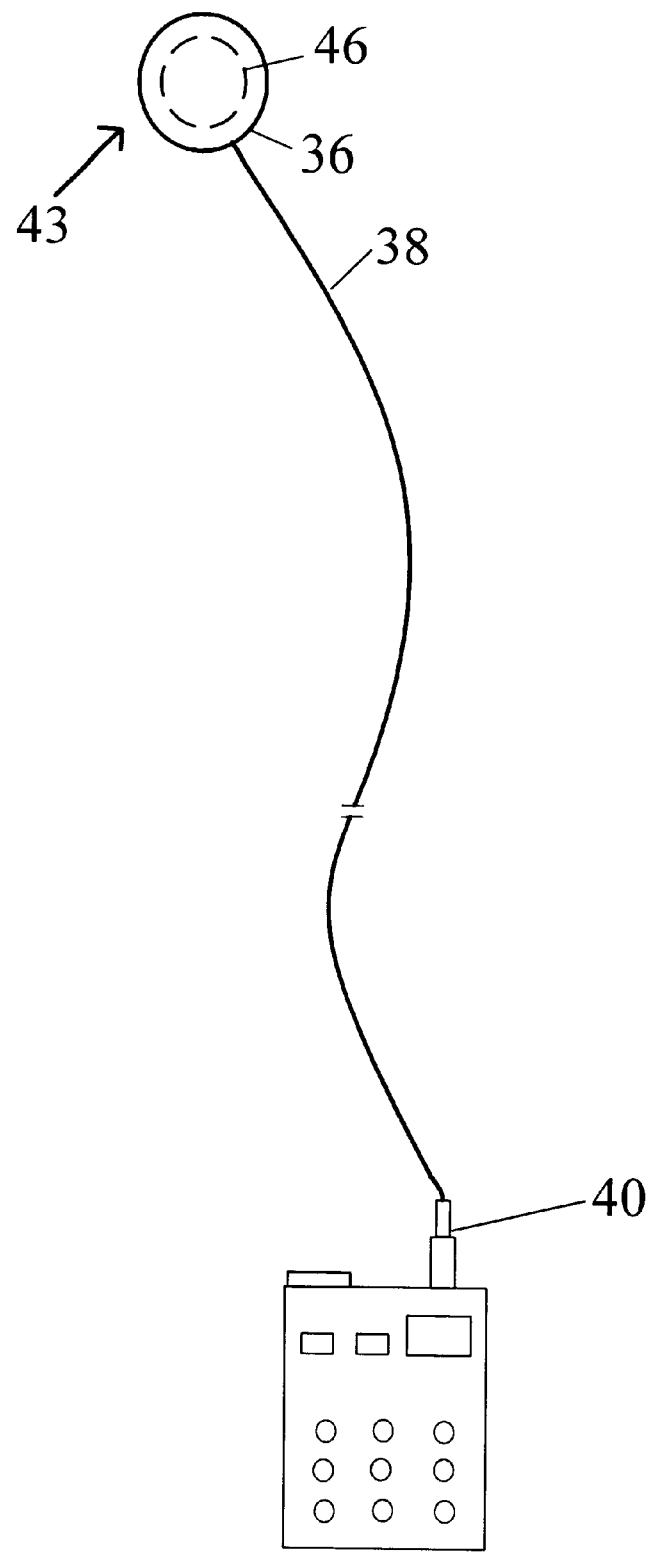
FIG. 12 is a diagram of an external patch and external pulse generator.

An external patch electrode 43 for inductive coupling is shown in FIG. 12. One end of the patch electrode contains the coil 46, and the other end has an adapter 40 to fit into the external stimulator 42. The external patch electrode 43, is a modification of the patch electrode available from TruMed Technologies, Burnsville, Minn.

Figure 13:
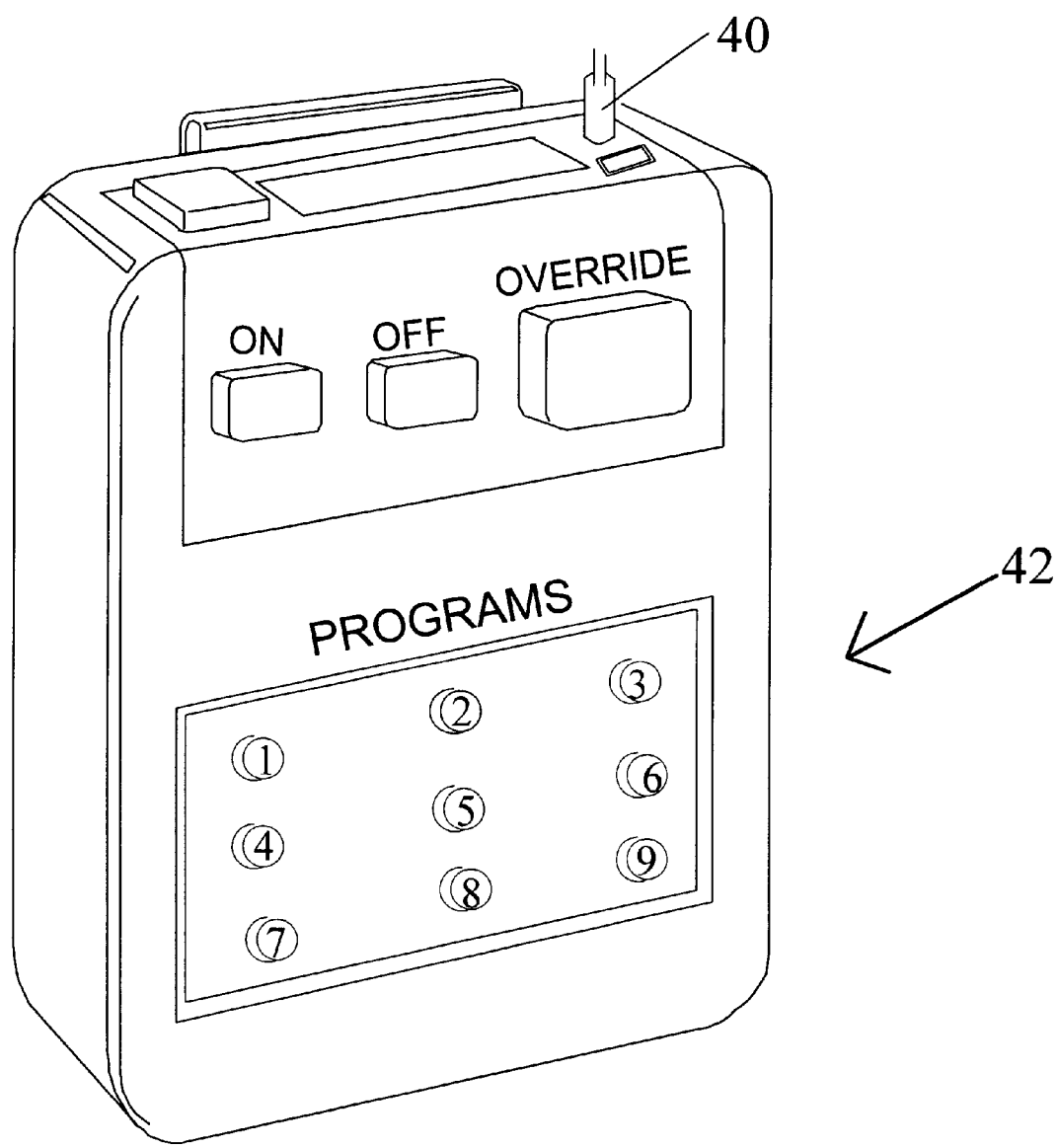
FIG. 13 is a prospective view of an external pulse generator.

FIG. 13 shows a front view of an external stimulator 42, which preferably is slightly larger than a conventional pager. The external stimulator 42 contains the circuitry and rechargeable or replaceable power source. The external stimulator 42 has two modes of operation. In the first mode of operation there are several pre-determined programs, preferably up to nine, which differ in stimulus intensity, pulse width, frequency of stimulation, and on-off timing sequence, e.g. "on" for 10 seconds and "off" for 50 seconds in repeating cycles. For patient safety, any number of these programs may be locked-out by the manufacturer or physician. In the second mode, the patient, or caretaker may activate the stimulation on at any time. This mode is useful for epileptic patients that have the characteristic "aura", which are sensory signs immediately preceding the convulsion that many epileptics have. When the device is turned on, a green light emitting diode (LED) indicates that the device is emitting electrical stimulation.

Pre-determined programs are arranged in such a way that the aggressiveness of the therapy increases from program #1 to Program #9. Thus the first three programs provide the least aggressive therapy, and the last three programs provide the most aggressive therapy.

The following are examples of least aggressive therapy.
Program #1:
1.0 mA current output, 0.2 msec pulse width, 15 Hz frequency, 15 sec ON time- 1.0 min OFF time, in repeating cycles.
Program #2:
1.5 mA current output, 0.3 msec pulse width, 20 Hz frequency, 20 sec ON time- 2.0 min OFF time, in repeating cycles.
The following are examples of intermediate level of therapy.
Program #5:
2.0 mA current output, 0.2 msec pulse width, 25 Hz frequency, 20 sec ON time- 1.0 min OFF time, in repeating cycles.
Program #6:
2.0 mA current output, 0.25 msec pulse width, 25 Hz frequency, 30 sec ON time- 1.0 min OFF time, in repeating cycles.
The following are examples of most aggressive therapy.
Program #8:
2.5 mA current output, 0.3 msec pulse width, 30 Hz frequency, 40 sec ON time- 1.5 min OFF time, in repeating cycles.

Program #9:

3.0 mA current output, 0.4 msec pulse width, 30 Hz frequency, 30 sec ON time- 1.0 min OFF time, in repeating cycles.

The majority of patients will fall into the category that require an intermediate level of therapy, such as program #5. The above are examples of the pre-determined programs that are delivered to the vagus nerve. The actual parameter settings for any given patient may deviate somewhat from the above.

Figure 14:
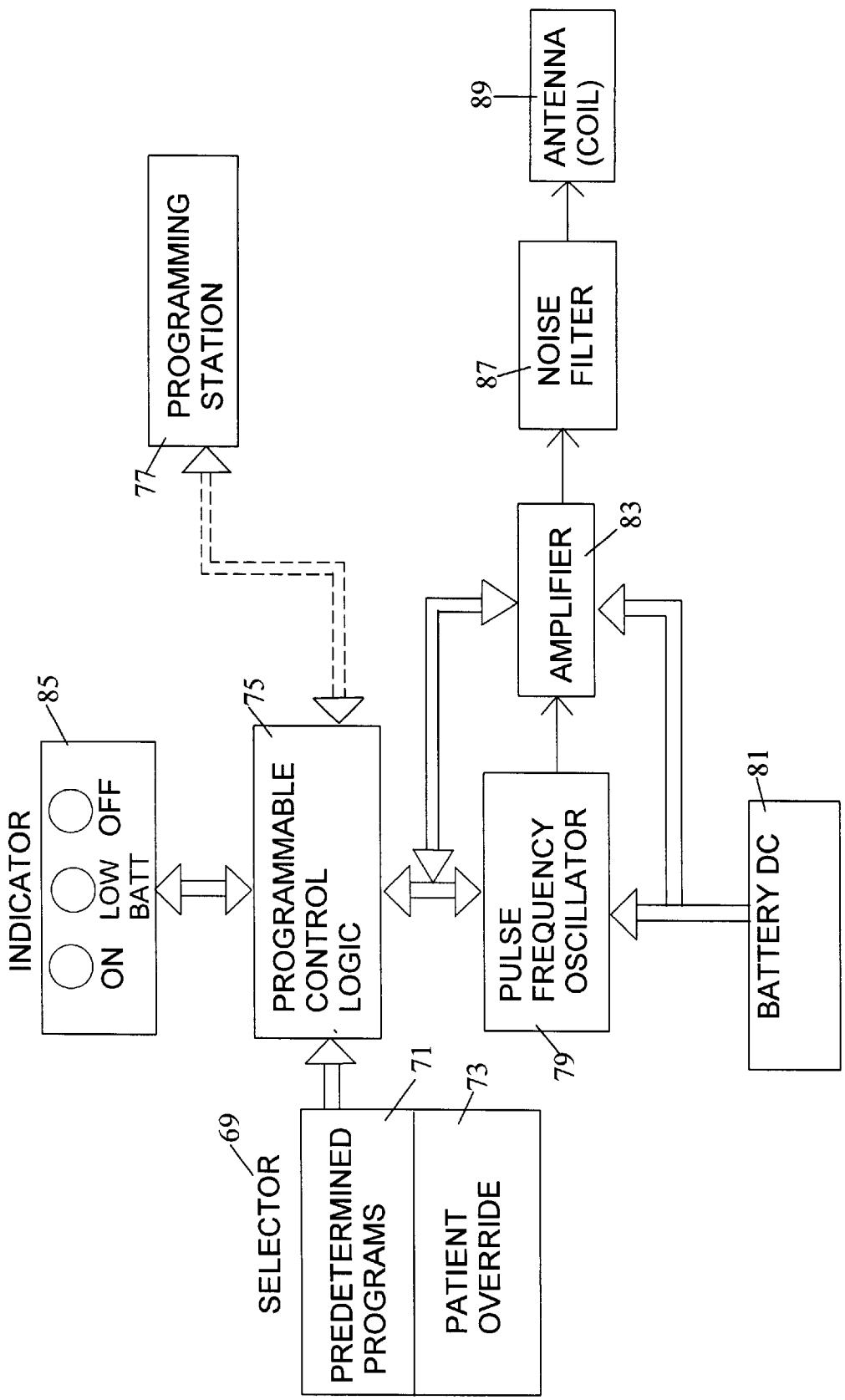
FIG. 14 is a flow diagram of the external pulse generator.

FIG. 14 shows a top level block diagram of the external stimulator 42. As previously mentioned, there are two modes of stimulation with the external stimulator 42. The first mode is a series of pre-determined standard programs 71, differing in the aggressiveness of the therapy. The second mode is patient override 73, where upon pressing a button, the device immediately goes into the active mode. The selector 69 which comprises of pre-determined programs 71 and patient override 73 feeds into programmable control logic 75. The programmable control logic 75 controls the pulse frequency oscillator 79. The output of the pulse frequency oscillator 79 is amplified 83, filtered 87 and provided to the external coil (antenina) 89, which is then transmitted to the implanted receiver 34 for stimulation of the nerve. The programmable control logic 75 is connected to an indicator 85 showing on-off status, as well as the battery status. The external stimulator 42 is powered by a DC battery 81. A programming station 77 provides the capability to download and change programs if the need arises.

Conventional integrated circuits are used for the logic, control and timing circuits. Conventional bipolar transistors are used in radio-frequency oscillator, pulse amplitude ramp control and power amplifier. A standard voltage regulator is used in low-voltage detector. The hardware and software to deliver these pre-determined programs is well known to those skilled in the art.

The fabrication of the lead-receiver 34 is designed to be modular. Thus, several different components can be mixed and matched without altering the functionality of the device significantly. As shown in FIG. 6, the lead-receiver 34 components are the proximal end 49 (containing coil 48, electrical circuitry 98, and case 78), the lead body 59 containing the conductor 65, and the distal electrode (cathode) 52. In the modular design concept, several design variables are possible, as shown in the table below.

Table of lead-receiver design variables

| Proximal End Circuitry and Return electrode | Lead body-Lumens | Lead body-Insulation materials | Lead-Coating | Conductor (connecting proximal and distal ends) | Electrode-Material | Distal End Electrode-Type |
|---|---|---|---|---|---|---|
| Bipolar | Single | Polyurethane | Lubricious (PVP) | Alloy of Nickal-Cobalt | Pure Platinum | Standard ball electrode |
| Unipolar | Double | Silicone | Antimicrobial | | Platinum-Iridium (Pt/Ir) alloy | Hydrogel electrode |
| | Triple | Silicone with Polytetrafluoroethylene (PTFE) | Anti-inflammatory | | Pt/Ir coated Titanium Nitride | Spiral electrode with |
| | Coaxial | | | | Carbon | Steroid eluting Fiber electrode |

Either silicone or polyurethane is suitable material for this implantable lead body 59. Both materials have proven to have desirable qualities which are not available in the other. Permanently implantable pacemaker leads made of polyurethane are susceptible to some forms of degradation over time. The identified mechanisms are Environmental Stress Cracking (ESC) and Metal Ion Oxidation (MIO). For this reason silicone material is slightly preferred over polyurethane.

Nerve-electrode interaction is an integral part of the stimulation system. As a practical benefit of modular design, any type of electrode described below can be used as the distal (cathode) stimulating electrode, without changing fabrication methodology or procedure significantly. When a standard ball electrode made of platinum or platinum/iridium is placed next to the nerve, and secured in place, it promotes an inflammatory response that leads to a thin fibrotic sheath around the electrode over a period of 1 to 6 weeks. This in turn leads to a stable position of electrode relative to the nerve, and a stable electrode-tissue interface, resulting in reliable stimulation of the nerve chronically without damaging the nerve.

Alternatively, other electrode forms that are non-traumatic to the nerve such as hydrogel, platinum fiber, or steroid elution electrodes may be used with this system. The concept of hydrogel electrode for nerve stimulation is shown schematically in FIG. 15. The hydrogel material 100 is wrapped around the nerve 54, with tiny platinum electrodes 102 being pulled back from nerve. Over a period of time in the body, the hydrogel material 100 will undergo degradation and there will be fibrotic tissue buildup. Because of the softness of the hydrogel material 100, these electrodes are non-traumatic to the nerve.

The concept of platinum fiber electrodes is shown schematically in FIG. 16. The distal fiber electrode 104 attached to the lead-receiver 34 may be platinum fiber or cable, or the electrode may be thin platinum fiber wrapped around Dacron polyester or Polyimide 106.

Figure 17:
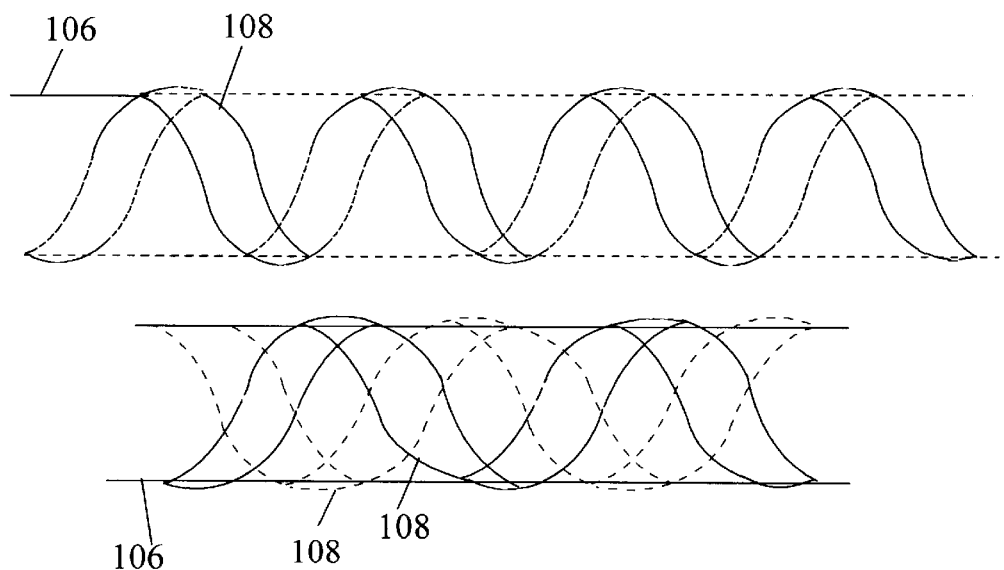
FIG. 17 is a diagram of a fiber electrode wrapped around Dacron polyester.
Figure 18:
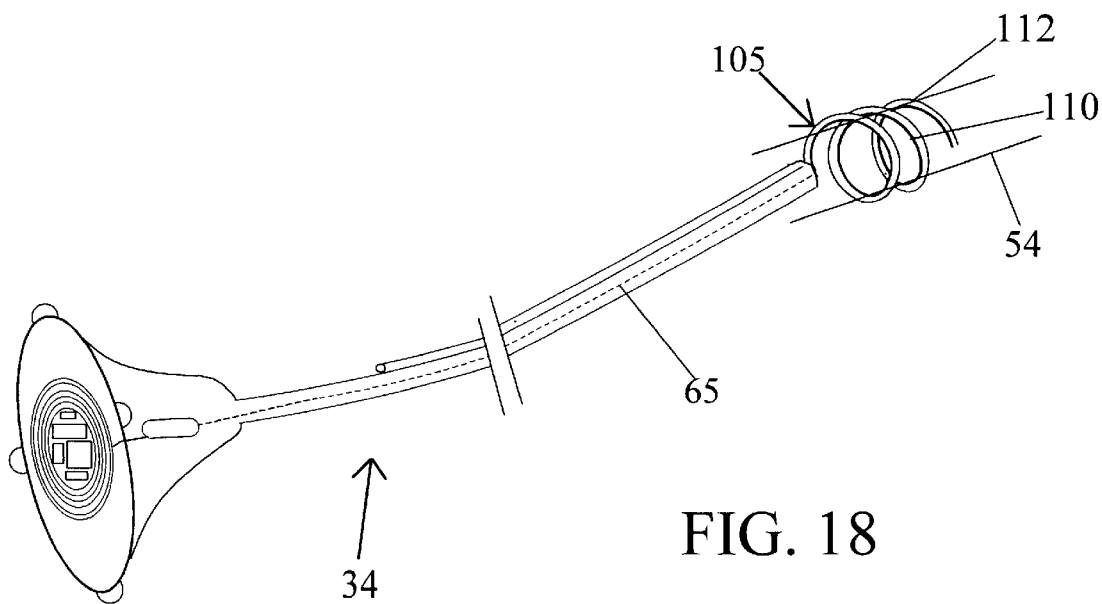
FIG. 18 is a diagram of a lead-receiver with a spiral electrode.

As shown in FIG. 17, the platinum fibers 108 may be woven around Dacron polyester fiber 106 or platinum fibers 108 may be braided. At implant, the fiber electrode 104 is loosely wrapped around the surgically isolated nerve, then tied loosely so as not to constrict the nerve or put pressure on the nerve. As a further extension, the fiber electrode may be incorporated into a spiral electrode 105 as is shown schematically in FIG. 18. The fiber electrode 110 is on the inner side of polyurethane or silicone insulation 112 which is heat treated to retain its spiral shape.

Figure 19:
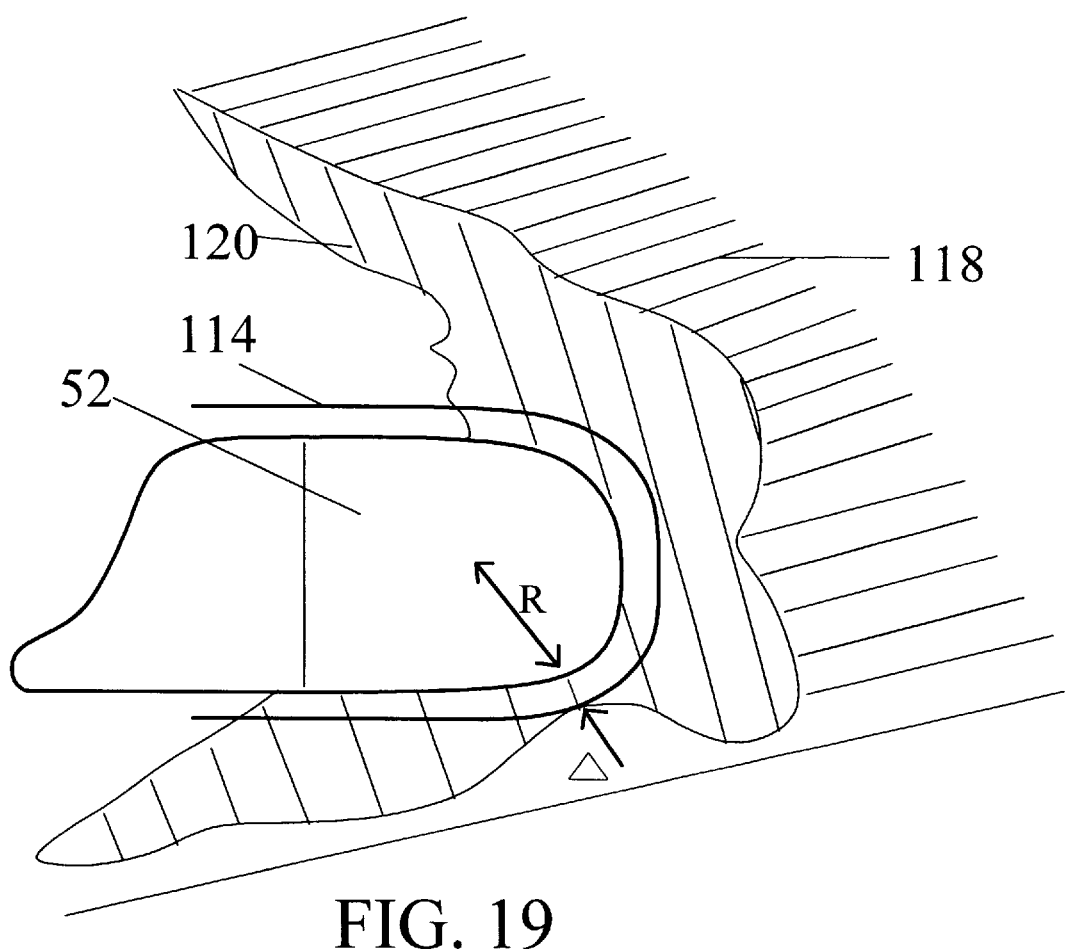
FIG. 19 is a diagram of an electrode embedded in tissue.

Alternatively, steroid elution electrodes may be used. After implantation of a lead in the body, during the first few weeks there is buildup of fibrotic tissue in-growth over the electrode and to some extent around the lead body. This fibrosis is the end result of body's inflammatory response process which begins soon after the device is implanted. The fibrotic tissue sheath has the net effect of increasing the distance between the stimulation electrode (cathode) and the excitable tissue, which is the vagal nerve in this case. This is shown schematically in FIG. 19, where electrode 52 when covered with fibrotic tissue becomes the "virtual" electrode 114. Non-excitable tissue is depicted as 120 and excitable tissue as 118. A small amount of corticosteroid, dexamethasone sodium phosphate commonly referred to as "steroid" or "dexamethasone" placed inside or around the electrode, has significant beneficial effect on the current or energy threshold, i.e. the amount of energy required to stimulate the excitable tissue. This is well known to those familiar in the art, as there is a long history of steroid elution leads in cardiac pacing application. It takes only about 1 mg of dexamethasone to produce the desirable effects. Three separate ways of delivering the steroid drug to the electrode nerve-tissue interface are being disclosed here. Dexamethasone can be placed inside an electrode with microholes, it can be placed adjacent to the electrode in a silicone collar, or it can be coated on the electrode itself.

Figure 20:
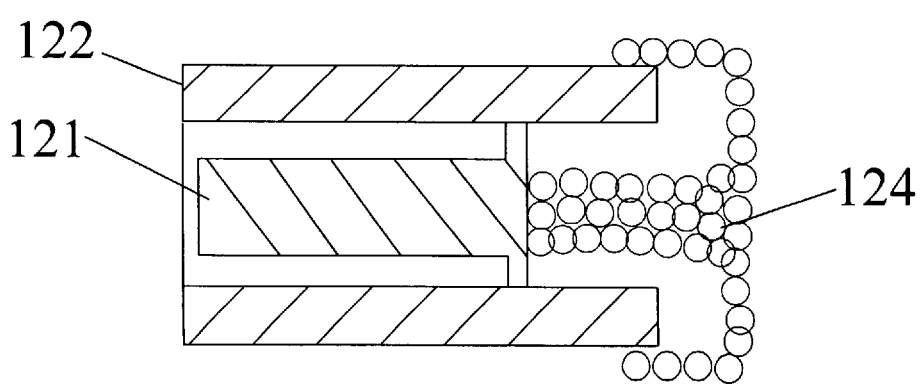
FIG. 20 is a diagram of an electrode containing steroid drug inside.

Dexamethasone inside the stimulating electrode is shown schematically in FIG. 20. A silicone core that is impregnated with a small quantity of dexamethasone 121, is incorporated inside the electrode. The electrode tip is depicted as 124 and electrode body as 122. Once the lead is implanted in the body, the steroid 121 elutes out through the small holes in the electrode. The steroid drug then has anti-inflammatory action at the electrode tissue interface, which leads to a much thinner fibrotic tissue capsule.

Another way of having a steroid eluting nerve stimulating electrode, is to have the steroid agent placed outside the distal electrode 52 in a silicone collar 126. This is shown schematically in FIG. 21. Approximately 1 mg of dexamethasone is contained in a silicone collar 126, at the base of the distal electrode 52. With such a method, the steroid drug elutes around the electrode 52 in a similar fashion and with similar pharmacokinetic properties, as with the steroid drug being inside the electrode.

Another method of steroid elution for nerve stimulation electrodes is by coating of steroid on the outside (exposed) surface area of the electrode. This is shown schematically in FIG. 22. Nafion is used as the coating matrix. Steroid membrane coating on the outside of the electrode is depicted as 128. The advantages of this method are that it can easily be applied to any electrode, fast and easy manufacturing, and it is cost effective. With this method, the rate of steroid delivery can be controlled by the level of sulfonation.

A schematic representation of the cross section of different possible lumens is shown in FIG. 23. The lead body 59 can have one, two, or three lumens for conducting cable, with or without a hollow lumen. In the cross sections, 132A–F represents lumens(s) for conducting cable, and 134A–C represents hollow lumen for aid in implanting the lead.

Additionally, different classes of coating may be applied to the implantable lead-receiver 34 after fabrication. These coatings fall into three categories, lubricious coating, antimicrobial coating, and anti-inflammatory coating.

The advantage of modular fabrication is that with one technology platform, several derivative products or models can be manufactured. As a specific practical example, using a silicone lead body platform, three separate derivative or lead models can be manufactured by using three different electrodes such as standard electrode, steroid electrode or spiral electrode. This is made possible by designing the fabrication steps such that the distal electrodes are assembled at the end, and as long as the electrodes are mated to the insulation and conducting cable, the shape or type of electrode does not matter. Similarly, different models can be produced by taking a finished lead and then coating it with lubricious coating or antimicrobial coating. In fact, considering the design variables disclosed in table 1, a large number ofcombinations are possible. Of these large number of possible combinations, about 6 or 7 models are planned for manufacturing. These include lead body composed of silicone and PTFE with standard ball electrodes made of platinum/iridium alloy, and silicone lead body with spiral electrode.

In addition to the neuromodulation of a cranial nerve such as the vagus nerve described above, neuromodulation of other nerves in the body can be performed. For example, neuromodulation of sacral nerve, which has beneficial effects for urinary incontinance, can be performed using an implantable lead-receiver and an external stimulator containing pre-determined program, where the two are inductively coupled. In such a case, the secondary coil wold be implanted in the lower abdominal region.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. An apparatus for electrical stimulation therapy for treatment of at least one of depression, migraine and neuropsychiatric disorders comprising:
  a) an implantable lead-receiver comprising a secondary coil and at least one electrode capable of stimulating a cranial nerve;
  b) an external stimulator comprising a power source, circuitry to emit electrical signals, at least two predetermined programs to control said electrical signals, and a primary coil;
  c) said primary coil of said external stimulator and said secondary coil of said implantable lead-receiver being capable of forming an electrical connection by inductive coupling,
  whereby said external stimulator is capable of controlling the stimulation of said cranial nerve.

2. The apparatus of claim 1 wherein said neuropsychiatric disorder comprises obsessive compulsive disorders.

3. The apparatus of claim 1, wherein said cranial nerve is the left vagus nerve.

4. The apparatus of claim 1, wherein said external stimulator comprises a patient override mechanism to manually activate said external stimulator.

5. The apparatus of claim 1, wherein said predetermined programs are capable of being modified to modify said electrical signals.

6. The apparatus of claim 1, further comprising a program selection mechanism wherein said at least two predetermined programs may be selectively operated.

7. The apparatus of claim 1, wherein said primary coil of said external stimulator is adapted to be in contact with the skin of the patient.

8. The apparatus of claim 1, wherein said lead-receiver comprises a lead body with at least one lumen, a lead body insulation, a conductor, at least one electrode and a coil.

9. The apparatus of claim 8, wherein said at least one lumen is selected from the group consisting of single, double, triple and coaxial lumens.

10. The apparatus of claim 8 wherein said lead body insulation is selected from the group consisting of polyurethane, silicone and silicone with polytetrafluoroethylene.

11. The apparatus of claim 8 wherein said lead body further comprises a coating selected from the group consisting of lubricious PVP, antimicrobial and anti-inflammatory coatings.

12. The apparatus of claim 8 wherein said electrode comprises a material selected from the group consisting of platinum, platinum/iridium alloy, platinum/iridium alloy coated with titanium nitride and carbon.

13. The apparatus of claim 8 wherein said electrode is selected from the group consisting of standard ball electrodes, hydrogel electrodes, spiral electrodes, steroid eluting electrodes, and fiber electrodes.

14. The apparatus of claim 1, wherein said electrical signals comprise at least one variable component selected from the group consisting of the current amplitude, pulse width, frequency and on-off timing sequence, and said at least two predetermined programs controls said variable component of said electrical signals.

15. A method to provide therapy for at least one of depression, migraine and neuropsychiatric disorders, comprising;
 a) providing an implantable lead-receiver comprising a secondary coil and at least one electrode to stimulate a cranial nerve;
 b) providing an external stimulator comprising circuitry to emit electrical signals, at least two programs to control said electrical signals, an external coil and a power supply;
 c) activating one of said at least two programs of said external stimulator to emit said electrical signals to said external coil;
 d) inductively transferring said electrical signals from said external coil of said external stimulator to said secondary coil of said lead-receiver;
 whereby said electrical signals stimulate said cranial nerve according to at least one of said at least two predetermined programs.

16. The method of claim 15, wherein said cranial nerve is the left vagus nerve.

17. The method of claim 15, wherein said cranial nerve is stimulated by bipolar stimulation.

18. The method of claim 15, wherein said cranial nerve is stimulated by unipolar stimulation.

19. The method of claim 15, wherein the step of activating one of said at least two predetermined programs is manually performed.

20. The method of claim 15, further comprising manually controlling said electrical signals to stimulate said cranial nerve.

21. The method of claim 15, wherein:
 a) said electrical signals comprise at least one variable component selected from the group consisting of the current amplitude, pulse width, frequency, and on-off timing sequence; and
 b) said at least two predetermined programs controls said variable component of said electrical signals.

22. The method of claim 15, further comprising manually disengaging said at least two predetermined programs.

23. A method for treating symptoms of depression, migraine or neuropsychiatric disorders comprising:
 a) selecting a predetermined program to control the output of an external stimulator;
 b) activating said external stimulator to emit electrical signals in accordance with said predetermined program; and
 c) inductively coupling said external stimulator with an implantable lead-receiver to stimulate a cranial nerve.

24. A method for treating symptoms of depression, migraine or neuropsychiatric disorders comprising:
 a) selecting one of at least two predetermined programs to control the output of an external stimulator;
 b) activating said external stimulator to emit electrical signals in accordance with said one of at least two predetermined programs; and
 c) inductively coupling said external stimulator with an implantable lead-receiver to stimulate a cranial nerve.

25. The method of claim 24, further comprising implanting beneath the skin of a patent said lead-receiver in direct electrical contact with said cranial nerve.

* * * * *